(12) United States Patent
Dube et al.

(10) Patent No.: US 6,434,329 B1
(45) Date of Patent: Aug. 13, 2002

(54) CONTROLLABLE CAMERA SUPPORT AND SYSTEM

(75) Inventors: Luc Dube, Laval; Glen Levesque, Montreal; Richard Hurteau, Montreal; Pierre A. Mathieu, Montreal, all of (CA)

(73) Assignees: L'Universite de Montreal; Centre Hospitalier de l'Universite de Montreal; Polyvalor S.E.C., all of Montreal (CA)

( * ) Notice: Subject to any disclaimer, the term of this patent is extended or adjusted under 35 U.S.C. 154(b) by 0 days.

(21) Appl. No.: 09/570,306

(22) Filed: May 12, 2000

(30) Foreign Application Priority Data

May 13, 1999 (CA) ................................................ 2272040

(51) Int. Cl.⁷ .................... G03B 29/00; G03B 17/00; A61B 19/00; B25J 11/00; B25J 19/00
(52) U.S. Cl. .................... 396/14; 396/428; 128/897; 901/14; 901/47
(58) Field of Search .................... 396/419, 428, 396/14; 248/176.3, 183.1, 186.2, 187.1; 901/14, 15, 41, 17, 18, 46, 47; 128/897

(56) References Cited

U.S. PATENT DOCUMENTS

| | | | | |
|---|---|---|---|---|
| 2,072,084 A | * | 3/1937 | Carey ........................... 396/14 |
| 4,166,543 A | * | 9/1979 | Dahlstrom .................. 340/521 |
| 4,356,534 A | | 10/1982 | Hattori ........................ 362/32 |
| 4,544,121 A | | 10/1985 | Komura ...................... 248/331 |
| 4,651,007 A | | 3/1987 | Perusek et al. .......... 250/363 S |
| 4,856,741 A | | 8/1989 | Schaefer ..................... 248/122 |
| 4,901,967 A | | 2/1990 | Petre ........................... 248/327 |
| 4,922,430 A | * | 5/1990 | Wavish ........................ 901/18 |
| 4,993,057 A | | 2/1991 | Runnells ..................... 378/197 |
| 4,993,683 A | | 2/1991 | Kreuzer ....................... 248/639 |
| 5,014,693 A | | 5/1991 | Wright, II et al. ...... 128/204.18 |
| 5,026,017 A | | 6/1991 | Kreuzer ....................... 248/324 |
| 5,078,140 A | * | 1/1992 | Kwoh .......................... 600/417 |
| 5,275,364 A | | 1/1994 | Burger et al. ............... 248/122 |
| 5,377,371 A | | 1/1995 | Foster ......................... 5/503.1 |
| 5,428,660 A | | 6/1995 | Daniel, Jr. ................... 378/197 |
| 5,436,542 A | | 7/1995 | Petelin et al. .............. 318/567 |
| 5,475,730 A | | 12/1995 | Galando ..................... 378/157 |
| 5,497,295 A | | 3/1996 | Gehly .......................... 362/32 |
| 5,615,854 A | | 4/1997 | Nomura et al. .......... 248/287.1 |
| 5,732,912 A | | 3/1998 | Nomura et al. .......... 248/187.1 |
| 6,023,289 A | * | 2/2000 | Oravecz et al. ............. 359/443 |

* cited by examiner

Primary Examiner—Christopher Mahoney
(74) Attorney, Agent, or Firm—Altera Law Group LLC

(57) ABSTRACT

A controllable camera support including a pivoting arm adapted to be rotatably connected to a pivot point defining a first rotational axis. The pivoting arm also defines a radial axis. The camera support also includes a camera holder mounted on the pivoting arm. The camera holder is displaceable along the radial axis. The camera further includes motors coupled to the pivoting arm and to the camera holder. The motors are adapted to impart rotational and radial motions to the camera holder. The camera support also includes a control device for controlling the motors. The invention also covers a system further including a focal adjustable, rotational, tilting camera mounted on the camera holder. When a target that is focused by the camera becomes obstructed, the control device is adapted to move the camera to another position all the while focusing on the target.

15 Claims, 26 Drawing Sheets

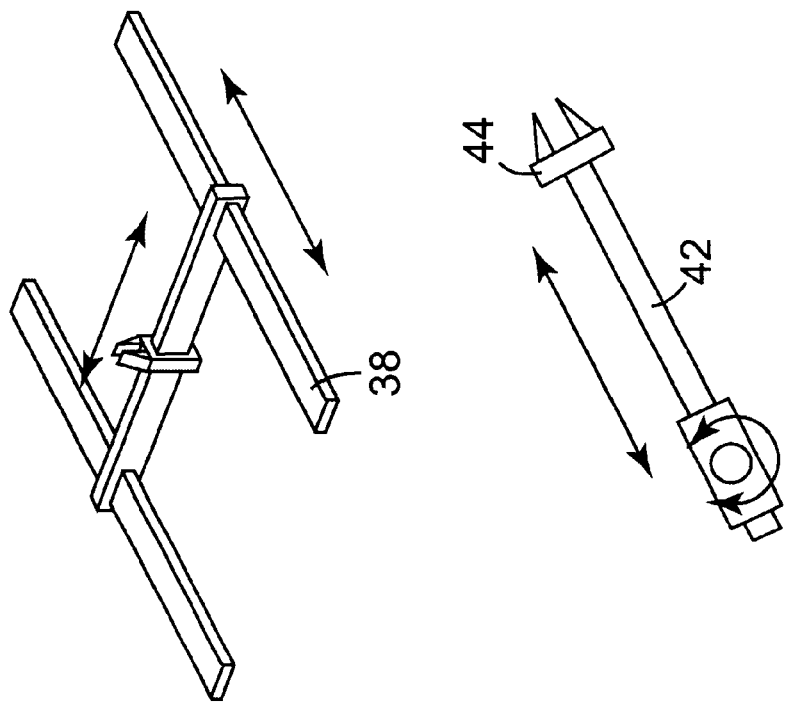
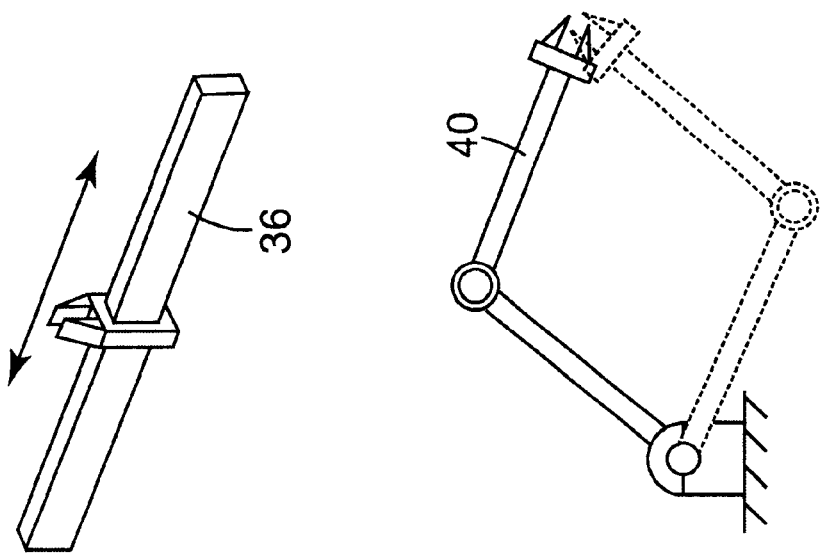
Fig. 4

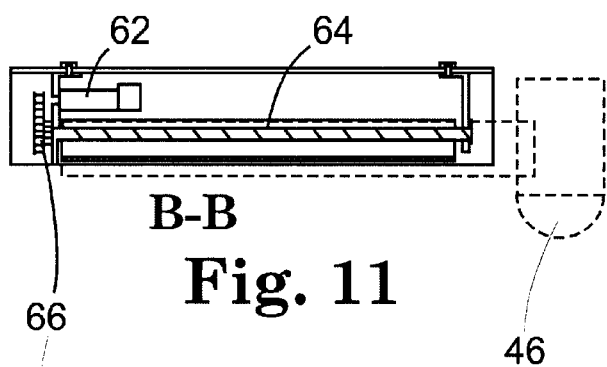
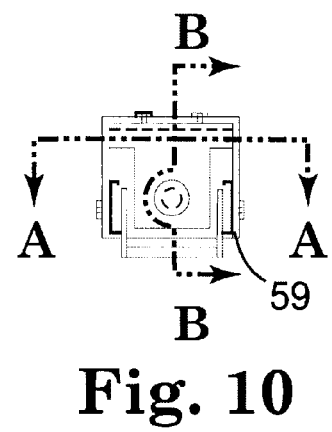
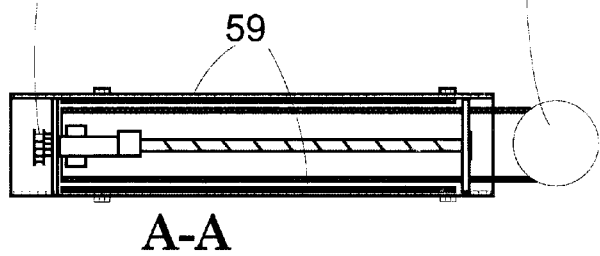
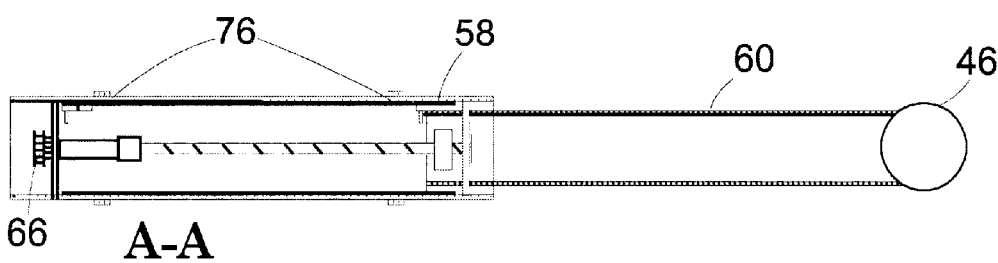

| i | $d_i$ | $a_i$ | $\alpha_i$ | $\theta_i$ |
|---|---|---|---|---|
| 1 | 0 | -L1 | $\pi/2$ | $\theta 1$ |
| 2 | L2+d2(t) | 0 | $-\pi/2$ | 0 |
| 3 | -L3- | 0 | $\pi/2$ | $\theta 3$ |
| 4 | 0 | 0 | $\pi/2$ | $\theta 4$ |
| 5 | d5(t) | 0 | 0 | 0 |

Fig. 26

CONTROLLABLE CAMERA SUPPORT AND SYSTEM

FIELD OF THE INVENTION

The present invention relates to a controllable camera support and system, used particularly in hospital operating rooms during surgery.

BACKGROUND OF THE INVENTION

The expansion of Internet has allowed service prices to go down while the demand and development of telecommunications technologies has increased exponentially. The technological developments in telecommunications have led to the formation of several regional and international committees in telemedicine, in particular the Telemedicine Committee of Canada and the International Telecommunications Committee. In general, telemedicine has the advantage of reducing costs of interchanging important medical information.

According to a publication (Sachs et al., 1995), a system called Spectro-Microscopy Collaboratory is used, in the Lawrence Berkley laboratory of the University of California, for observing the laboratory and making experiments at a distance. A visualisation system is used for selecting different cameras in an experiment room and changing their orientation. This system is also used by the University of Wisconsin-Milwaukee for making experiments in the Lawrence Berkley laboratory of California.

Another system has ben developed at the University of Tokyo in collaboration with National Hospital of Fukuyama (Mitsuishi et al., 1995). This system is a very complex robotic system for observing and controlling a surgical robot from a distance. The system comprises a slave type manipulator and a slave surgical microscope which is moved correspondingly with the tip of a device used by a user. This system has been successful in performing an anastomose of a blood vessel having a diameter of less than 1 mm in a rat (Mitsuishi).

These aforementioned technologies are quite evolved but are not directly applicable for use in an operating room. In particular, these solutions are too complicated and expensive to be used in an operating room.

SUMMARY OF THE INVENTION

An object of the present invention is to provide a controllable camera support and a system which are relatively simple and less expensive than those known in the art.

Another object of the present invention is to provide a algorithm and method that will allow a distant observer to control the camera support and the camera.

Another object of the present invention is to provide a controllable camera support comprising:

a pivoting arm adapted to be rotatably connected to a pivot point defining a first rotational axis, the pivoting arm defining a radial axis;

a camera holder mounted on the pivoting arm, the camera holder being displaceable along the radial axis;

motor means coupled to the pivoting arm and to the camera holder, the motor means adapted to impart rotational and radial motions to the camera holder; and control means for controlling the motor means.

Another object of the present invention is to provide a camera system comprising:

a pivoting arm adapted to be rotatably connected to a pivot point defining a first rotational axis, said pivoting arm defining a radial axis;

a camera holder mounted on said pivoting arm, said camera holder being displaceable along said radial axis;

a focal adjustable, rotational, tilting camera mounted on said camera holder, said camera defining a second rotational axis parallel to said first rotational axis about which said camera may rotate by means of an camera rotation motor, said camera defining a third rotational axis perpendicular to said first rotational axis about which said camera may tilt by means of a camera tilting motor, said camera including a focal adjustment mechanism;

motor means coupled to said pivoting arm and to said camera holder, said motor means adapted to impart rotational and radial motions to said camera holder; and control means for controlling said motor means, said camera rotation motor, said camera tilting motor, and said focal adjustment mechanism.

Another object of the present invention is to provide a camera system comprising:

a pivoting arm adapted to be rotatably connected to a pivot point defining a first rotational axis, said pivoting arm defining a radial axis;

a camera holder mounted on said pivoting arm, said camera holder being displaceable along said radial axis;

a focal adjustable, rotational, tilting camera mounted on said camera holder, said camera defining a second rotational axis parallel to said first rotational axis about which said camera may rotate by means of an camera rotation motor, said camera defining a third rotational axis perpendicular to said first rotational axis about which said camera may tilt by means of a camera tilting motor, said camera including a focal adjustment mechanism, said camera focusing on a target;

motor means coupled to said pivoting arm and to said camera holder, said motor means adapted to impart rotational and radial motions to said camera holder; and control means for controlling said motor means, said camera rotation motor, said camera tilting motor, and said focal adjustment mechanism;

wherein when the target focused by the camera becomes obstructed by an obstruction, said control means is adapted to move said camera to another position all the while focusing on said target, whereby as said camera moves, said target is always focused by said camera so that said camera can be moved to another position where the obstruction does not obstruct said camera.

BRIEF DESCRIPTION OF THE DRAWINGS

The invention as well as its numerous advantages will be better understood by the following non restrictive description of preferred embodiments made in reference to the appended drawings in which:

FIG. 4 are different possible embodiments of the controllable arm support according to the present invention;

FIG. 10 is a front view of the pivoting arm shown in FIG. 8;

FIG. 11 is a side section view along line B—B of the pivoting arm shown in FIG. 10 and a radial motor mechanism;

FIG. 12 is a top section view along line A—A of the pivoting arm shown in FIG. 11;

FIG. 13 is a top section view along line A—A of the pivoting arm shown in FIG. 11 in an extended position;

FIG. 26 is a table of the parameters of the system;

DETAILED DESCRIPTION OF THE INVENTION

Figure 1:
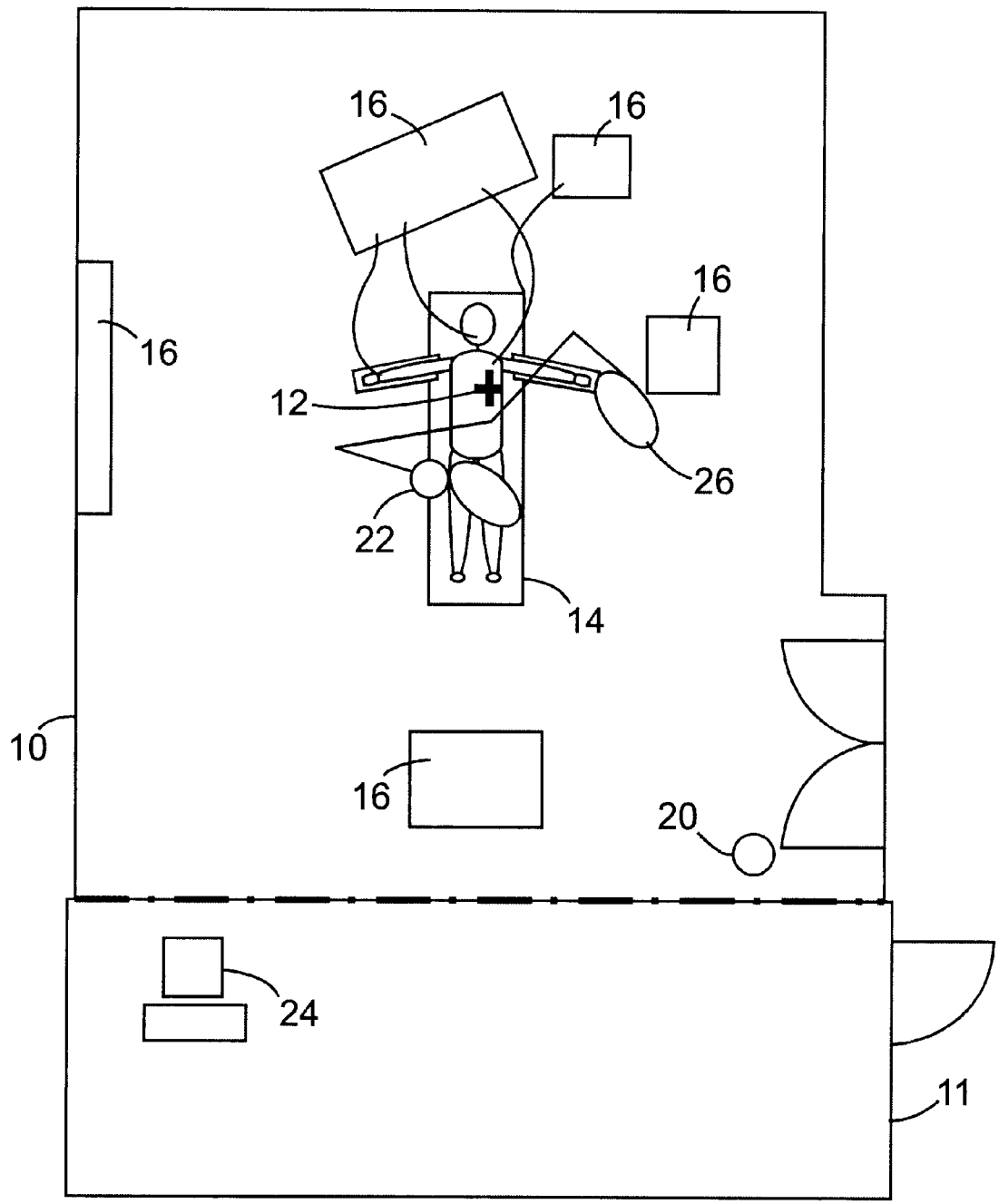
FIG. 1 is a top view of an operating room.

Referring to FIG. 1, there is shown a top view of a sterile operating room 10 and an adjacent non-sterile room 11 where students can observe an operation. A patient 12 is located on an operating table 14, normally at the center of the operating room 10. Several bombardment instruments or medical equipment 16 are also located in the room, such as monitoring devices, an anaesthesia table, electro-surgical devices, etc.

Figure 2:
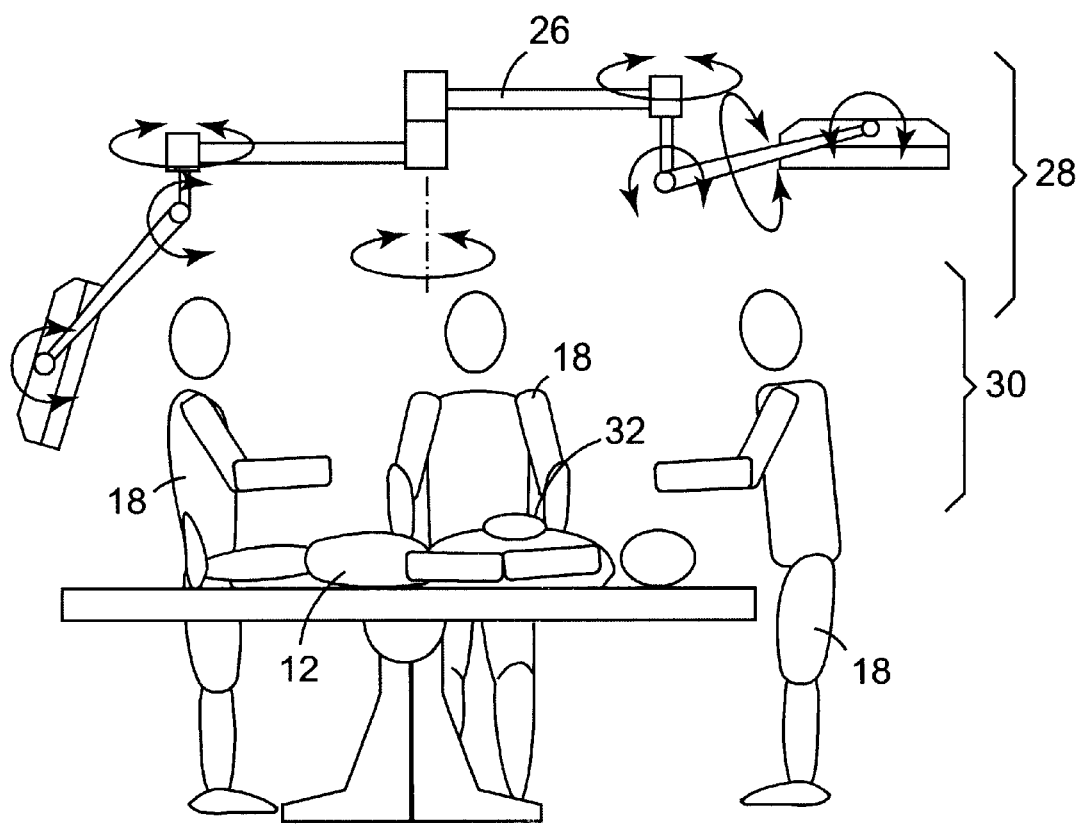
FIG. 2 is a side view of an operating room.

Referring to FIG. 2, the patient 12 is surrounded by a medical team compensated of several staff members 18. Students may also observe the operation, and more specifically the surgical site, directly in the operation room 10, or indirectly through a glass window separating the operating room 10 from the observation room 11.

Referring to FIGS. 1 and 2, another indirect way of observing the operation room 10 is through a pair of cameras 20, 22 which are connected to a monitor 24 in the observation room 11. The cameras 20, 22 are focused onto the surgical site or any object of interest in the room 10 such as an ECG on an anaesthesia monitor or X-ray. The first camera 20 is a stationary camera which is located in a corner of the operating room 10. The second camera 22 is mounted on a surgical lamp structure 26 located just above the patient 12. Although the lamp structure 26 can be moved, it tends to be almost stationary once it has been adjusted and the operation has begun. Therefore, these cameras 20, 22 are prone to be obstructed by the staff members 18 as these move in front of the camera and around the patient 12.

There is a need to control the positioning of the second camera 22 so that obstructions can be avoided. A special software must be used in order to control a camera support and a camera mounted thereon. This software is especially useful in remote control applications such as teleconsulting and telemedicine.

The software used in developing the controlling commands in this invention is the Labview™ software. Labview uses a graphical program language, called "G", which has a block diagram form. Such programming language is particular because it allows building "virtual instruments". The structure of the "virtual instruments" may be divided in two parts: a front interactive window called front panel, and a source code window associated with the front interactive window. Each virtual instrument may have its own virtual instruments making this language hierarchical and modular.

A hardware component is also necessary for linking the above mentioned software component to the controllable camera support. In this context, the acquisition card used is the DAQcard-1200 from National Instrument. This card has 8 inputs and two analog outputs with 12-bit resolution, 24 digital inputs/outputs and 3 16-bit counters. The software and the acquisition card are installed in a portable PC which may be a IBM Pentium 133 MHz.

The camera used with the controllable camera support has a panoramic unit with a motorized integrated lens. The movements allowed by the panoramic unit are an infinite azimuth rotation (endless pan) and a tilt of 0 to 90 degrees going from a horizontal position to a vertical position.

Technologies for transmitting images have significantly evolved since the introduction of PC based multimedia technologies. These include a transmission protocol for transmission from a local video image system to a remote location. These technologies also include a protocol for remote control of robotic systems.

An aspect of the present invention is to provide a controllable camera support which is able to move the camera in different types of operating rooms but it should not be limited such an application. The controllable camera support may be used for industrial teleconsultation applications or any particular site where remote observation is necessary (e.g. nuclear power plant).

The controllable camera support should also minimize collisions or contacts with the medical equipment 16, the surgical lamps 26, or the medical staff members 18 while allowing displacement of the camera so as to obtain the best vision on the operating site or target point 32.

Referring back again to FIG. 2, looking down from the ceiling towards the target 32, there are two obstructing obstacles called layers 28, 30 that may bloc access to the target 32. The first layer includes the surgical lamps 26 and the second layer 30 includes the staff members 18.

In order for a camera mounted on the ceiling of the operating room to view the target 32, it must traverse both of these layers 28, 30. The visual field that can reach the target 32 is a straight line passing through openings in these layers 28, 30.

Figure 3:
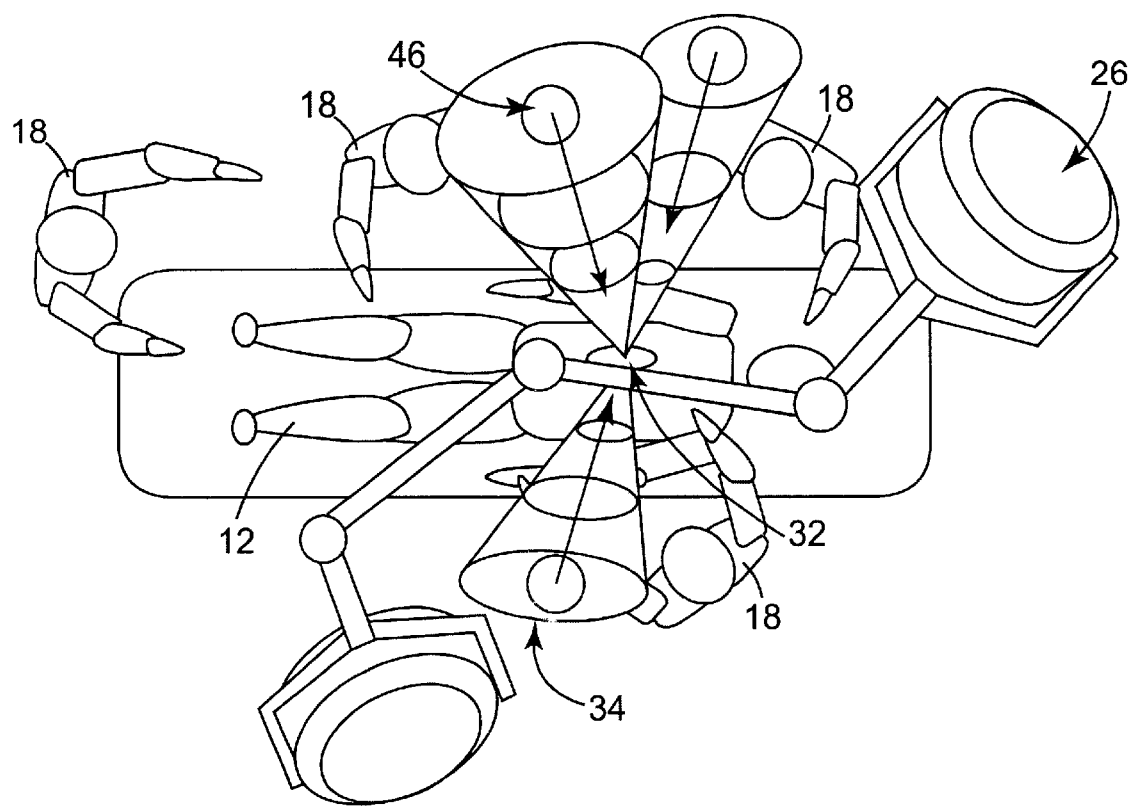
FIG. 3 is another top view of the operating room.

Referring to FIG. 3, a series of cones 34, which move as a function of time and of the type of surgery, represent some possible visual fields of the movable camera 46 toward the target 32.

The target may be fixed in space, as is normally the case in a surgical operation, or it may move. If the target moves, an additional system is necessary in the camera system in order to follow the target. For example, the target may be marked so that a computer system may be able to detect a movement thereof.

Another important aspect of the invention concerns the capability of the camera system to maintain a focus on a target while at the same time the camera and the support move in sapce in a predetermined path configuration. For example, the camera and camera support may follow an S-shape path in space while still focusing on the target.

Referring to FIG. 4, several different configurations may be used for a controllable camera support in a planar portion of space above the target 32. A first one is a linear support 36 having one degree of freedom. This option is not very flexible. The second one is a table type support 38 having two degrees of freedom. It is however cumbersome and may be hardly adaptable in an operating room. The third and fourth camera supports shown are robotic arm systems 40, 42. Of the numerous two degrees of freedom configurations, these two 40, 42 seem more appropriate for solving the problem at hand. The planar rotation-rotation camera support 40 is not the most compact and may be difficult to manipulate between obstacles. Furthermore, such a support 40 is redundant, i.e. different positions of its arms may reach the same point in the plane (as shown by the dotted lines).

The preferred controllable camera support is the rotation-radial type mechanism 42 which has a single pivoting arm and is not redundant. The rotational-radial type mechanism is also called polar type mechanism because the position of its camera holder 44 may be determined by orientation and radius information. The preferred controllable camera support 42 also has the advantage of being compact, while being able to double, triple, or quadruple its length.

The flexibility of the chosen system not only lies in the chosen mechanism but also in its position inside the operating room. An optimal system may be based on the combination of the chosen camera support and its strategic position to offer the most views on the target 32. It is advantageous to choose a camera support and a position for it that avoids the surgical lamps structures 26.

Referring to FIG. 3, the surgical lamp structures 26 are generally formed of an articulated mechanical arm onto which a lamp is fixed. Such surgical lamp structures 26 have several degrees of freedom (4 to 6) and allow great flexibility in their positioning above the target 32 (which is alternatively called surgical site). Such lamp structures 26 may have several arms each supporting its own lamp.

These surgical lamps structures 26 have a central axis which may be advantageously used for mounting the rotation-radial type mechanism 42.

Figure 5:
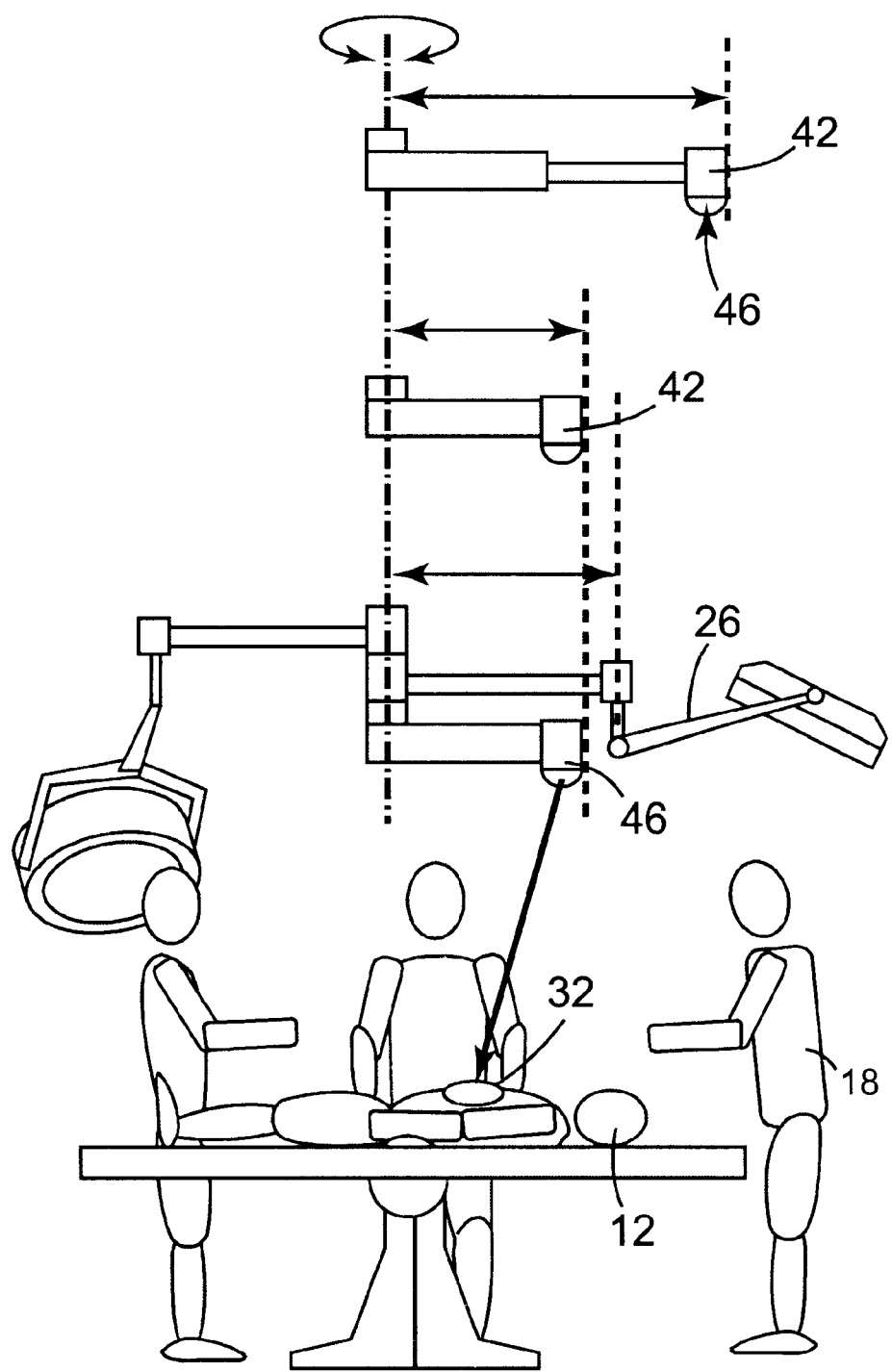
FIG. 5 is a side view of an operating room incorporating the controllable camera support.

Referring to FIG. 5, the illustrated camera support 42 is mounted in different positions. The highest position shows the camera support 42 mounted on the ceiling of the operating room 10. Another suitable position is with the camera support 42 mounted on the surgical lamp structure 26.

Figure 6:
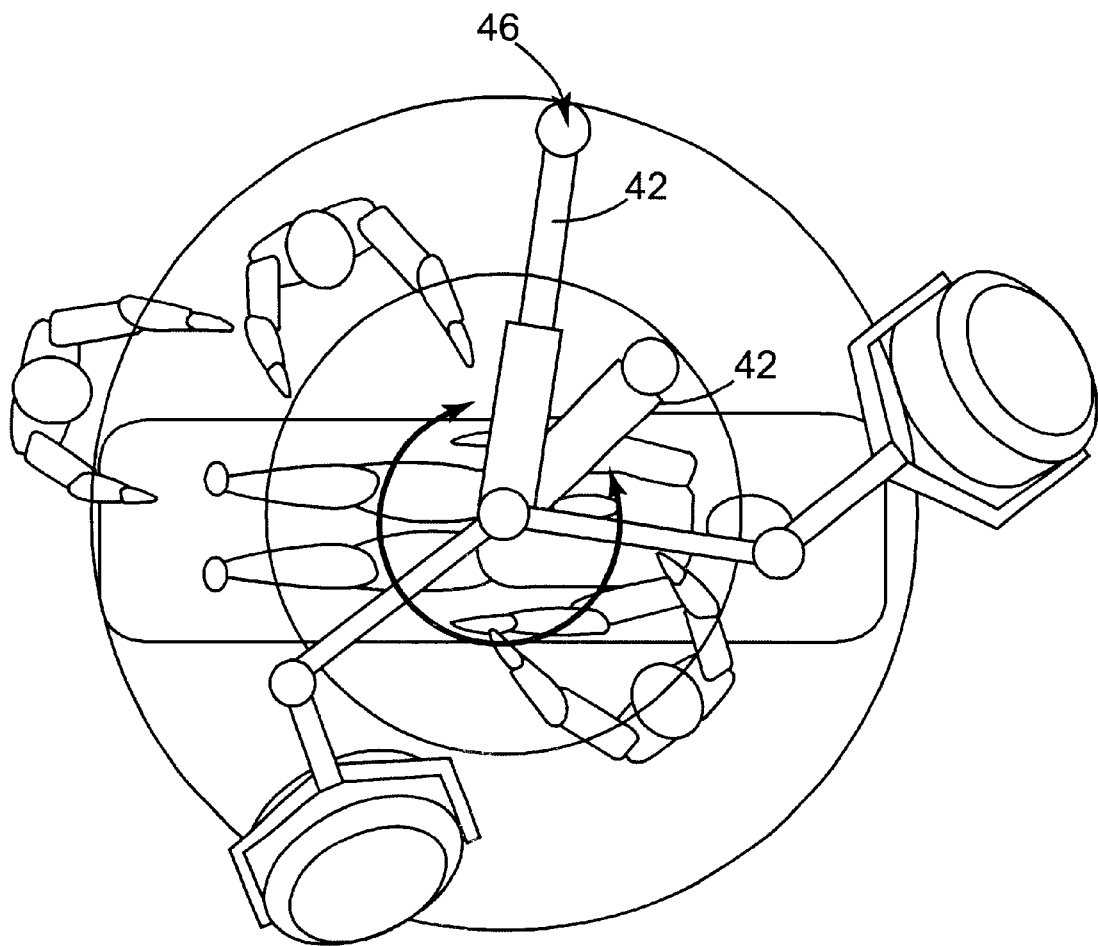
FIG. 6 is a top view of an operating room incorporating the controllable camera support.

Referring to FIG. 5 and to FIG. 6, the camera support 42 is also shown in an maximum extension position and in a maximum extension position.

The positioning of the camera support 42 under the lamp structure 26 is strategic because it avoids the first layer 28 completely.

Figure 7:
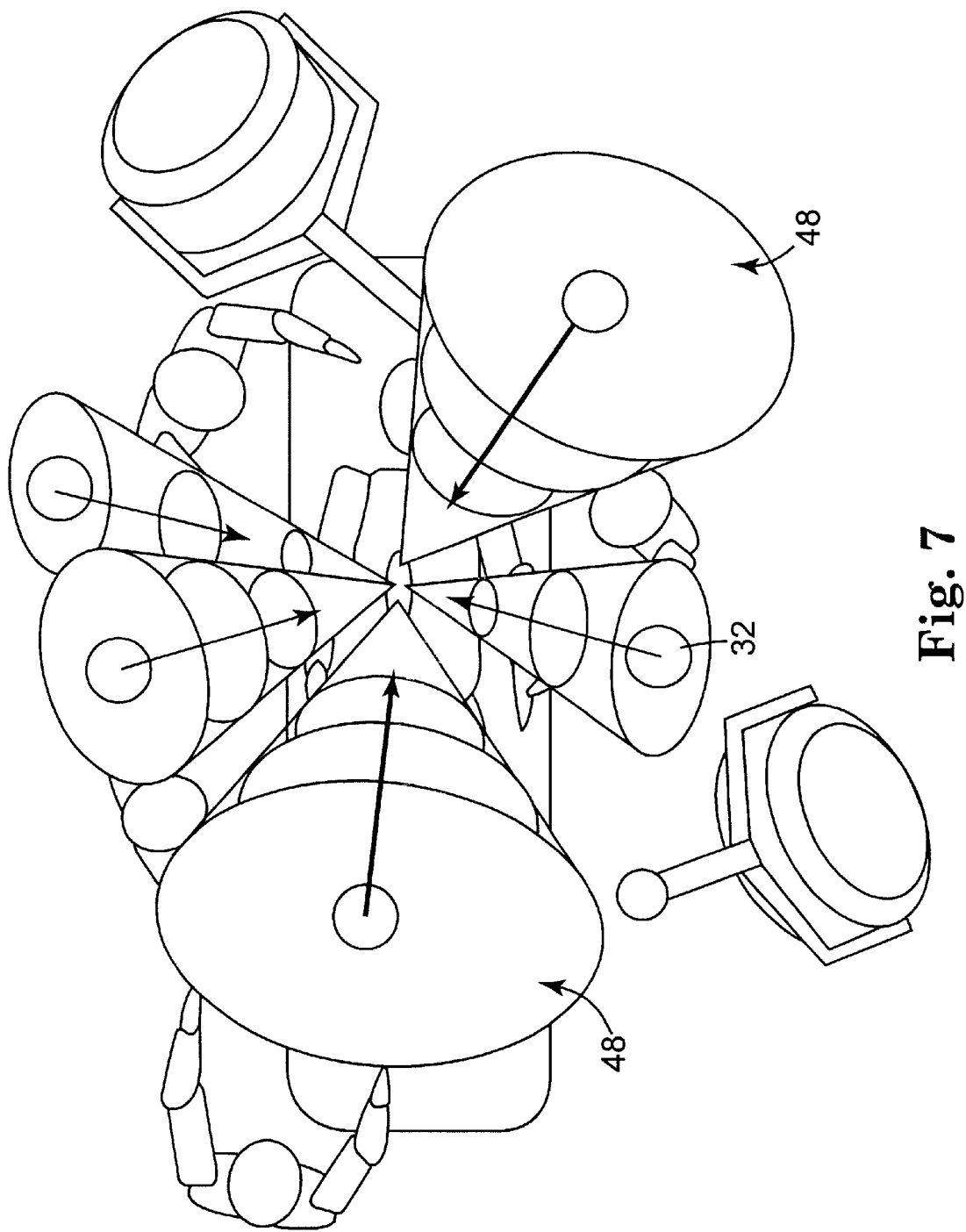
FIG. 7 is a top view of an operating room with visual field cones.

Referring to FIG. 7, the new cones 48, which represent the visual fields when the camera support is under the lamp structure 26, are bigger than the former cones 32 shown in FIG. 3.

Figure 8:
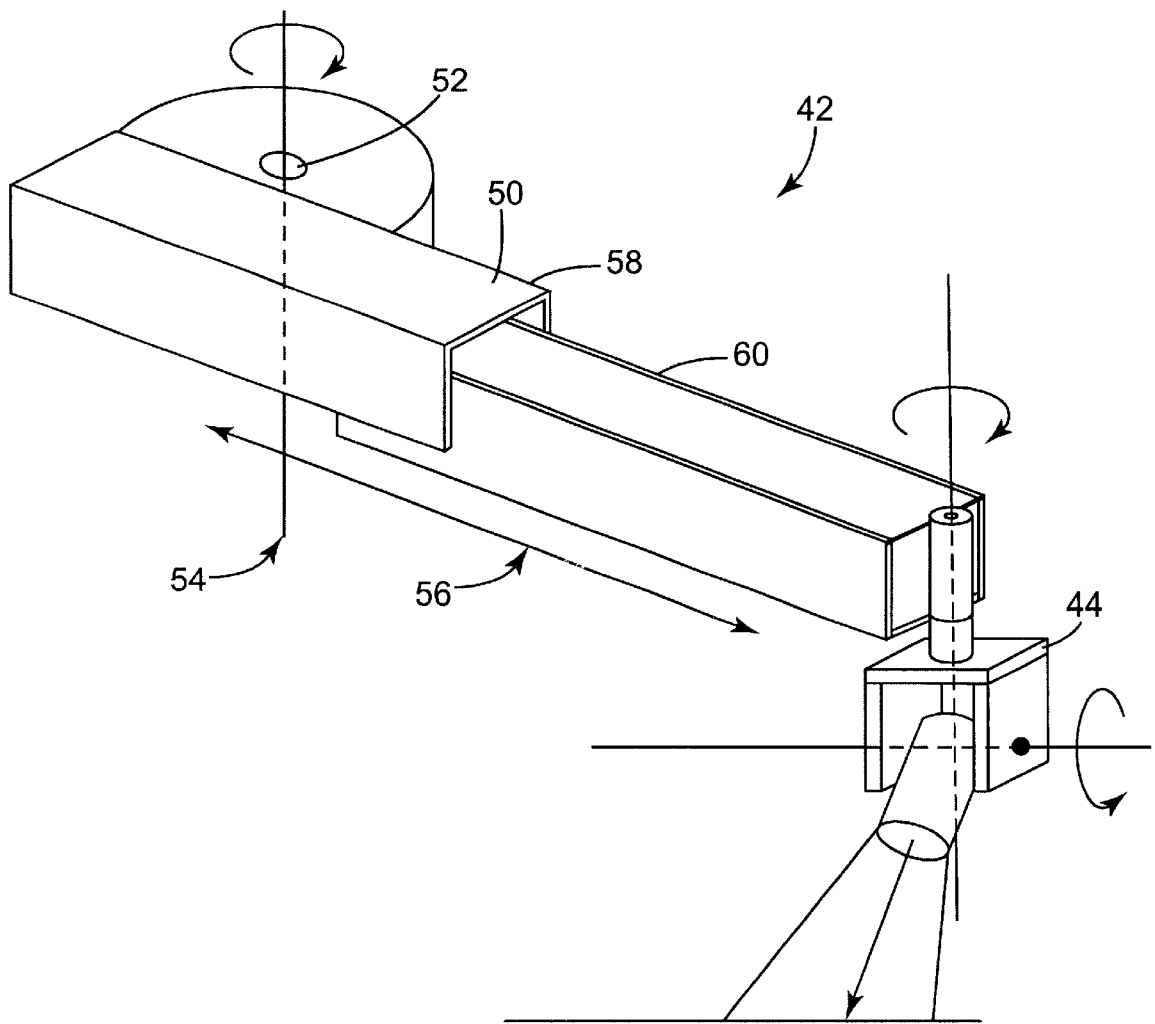
FIG. 8 is a perspective view of the controllable camera support according to a preferred embodiment of the invention.

Referring to FIG. 8, there is shown a controllable camera support 42 according to a preferred embodiment of the present invention. The controllable camera support 42 has a pivoting arm 50 which is adapted to be rotatably connected to a pivot point 52 which defines a first rotational axis 54. The pivoting arm 50 also defines a radial axis 56.

A camera holder 44 is mounted on the pivoting arm 50. The camera holder 44 is adapted to be displaceable along the radial axis 56. In the illustration, the camera holder 44 is fixed at an end of the pivoting arm 50, but the camera holder 44 may also be mounted, for example, on a set of rollers enabling it to effect a relative movement along the radial axis 56 with respect to the pivoting arm 50. The coupling of the camera holder 44 to the pivoting arm should be construed to include any type of prismatic movement. The term prismatic movement is widely used in robotics and is equivalent to the radial movement defined above.

Motor devices, which will be later exemplified, are coupled to the pivoting arm 50 and to the camera holder 44. These motor devices are adapted to impart rotational and radial motions to the camera holder 44.

The controllable camera support 42 also includes a control system for controlling the motor devices.

Figure 9:
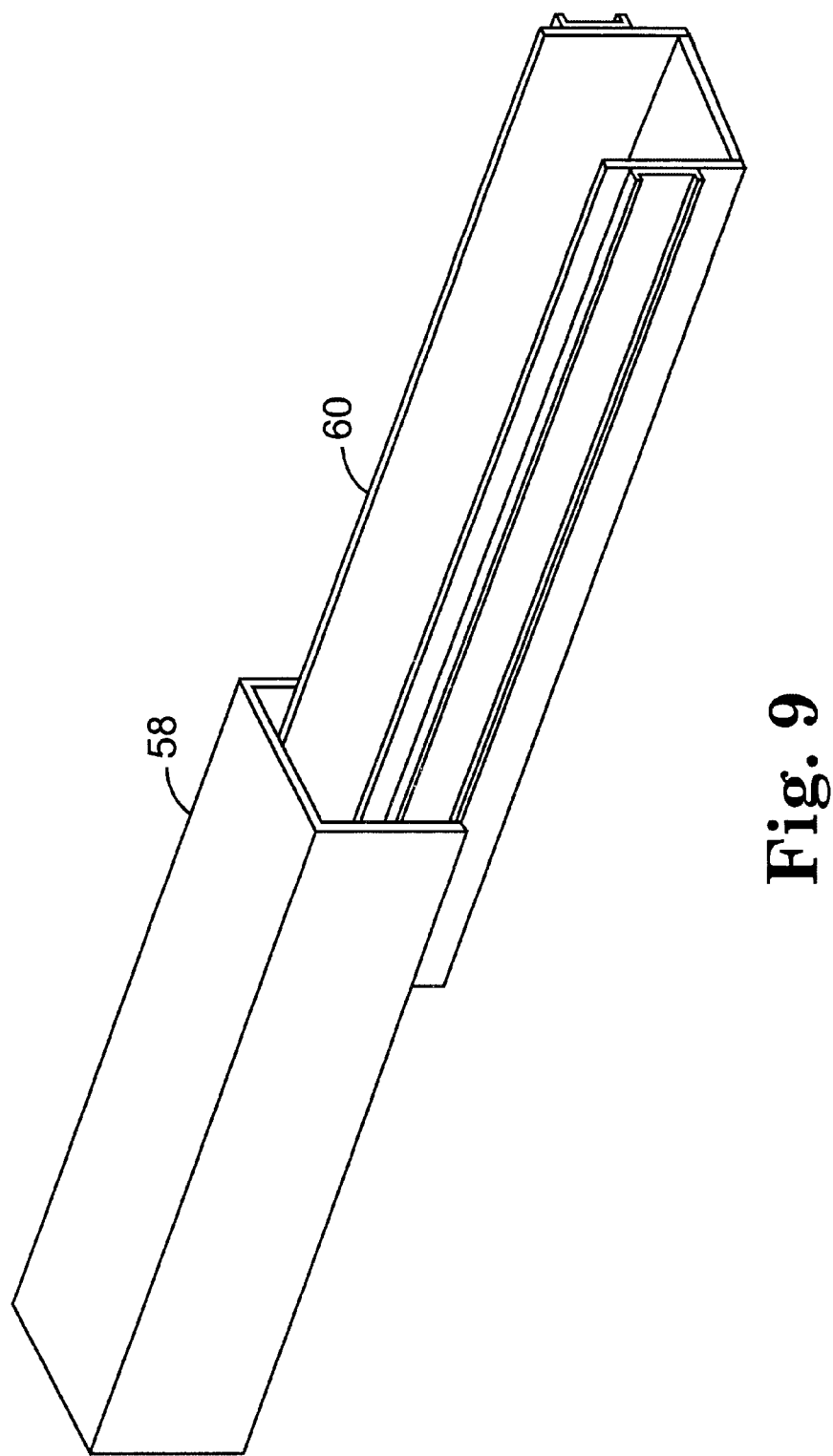
FIG. 9 is a perspective view of the pivoting arm of the controllable camera support shown in FIG. 8.

Referring to FIG. 9, the pivoting arm 50 comprises a first portion 58 and a second portion 60. The first portion 58 is connected to the pivot point 52 and the second portion 60 is adapted to effect a relative movement with respect to the first portion along the radial axis 56. As illustrated, a simple rail system 59 may be used wherein one portion 60 slides under another 58.

As mentioned above, the above structure is for illustration purposes only and the invention should cover any prismatic movement of a controllable camera support.

The pivoting arm 50 may also contain an additional portion adapted to effect a relative movement with respect to the first and second portions 58, 60, thereby forming a telescoping arm.

Referring to FIGS. 10, to 13, there is illustrated the motor device for imparting radial motion to the camera holder 44. The motor device comprises a radial motor 62 coupled to a endless screw mechanism 64. A gear and chain mechanism 66 couples the radial motor 62 to the endless screw 64. Thus, the first and second portions 58, 60 may slide with respect to each other so as to extend or retract the movable camera 46.

Referring to FIGS. 14 to 17, there is shown the motor device for imparting rotational motion to the pivoting arm 50. The motor device comprises a rotational motor 68. A fixed gear 70 is coupled to the pivot point 52. The rotational motor 68 is coupled to the fixed gear 70 through a chain 72. The motor is directly coupled to a mobile gear 74.

The rotational motor 70 is coupled to a slip clutch mechanism for disengaging the rotational motor 70 from the pivoting arm 50. Similarly, the radial motor 62 may be provide with such a slip clutch mechanism. Therefore, whenever an obstacle or any force opposes the movement of the camera support, the motors will be disengaged and will not cause any damage to the system or immediate environment.

Figure 14:
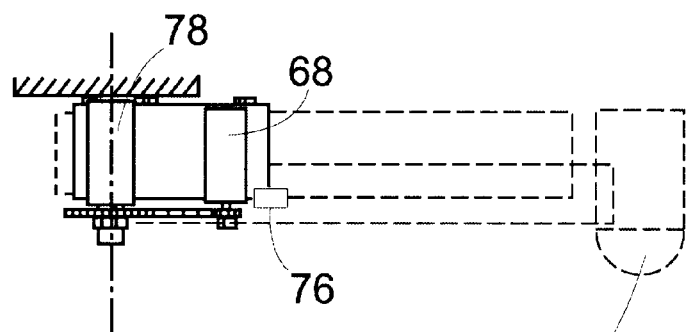
FIG. 14 is a side view of the rotational motor mechanism of the pivoting arm.
Figure 16:
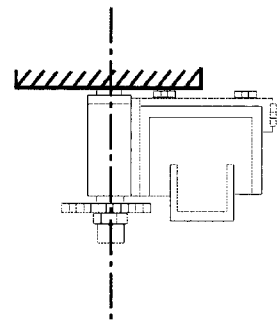
FIG. 16 is another detailed view of FIG. 14.
Figure 17:
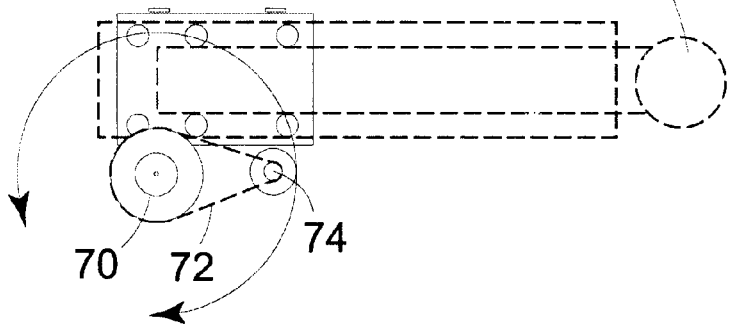
FIG. 17 is a top view of the rotational motor mechanism shown in FIG. 14.

Referring to FIGS. 13 and 14, the camera support also includes another security component by providing limit switches 76 which is adapted to shut down power to the radial and rotational motors 62, 68. The limit switch 76 is adapted to shut down the motors when the pivoting arm reaches a maximum or minimum length when extended or retracted, or when it reaches a certain rotation position.

Figure 15:
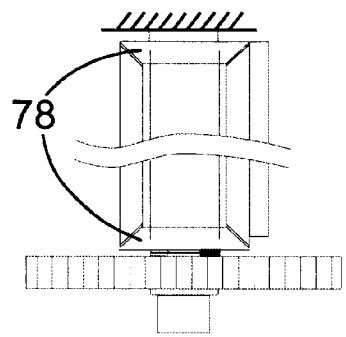
FIG. 15 is a detailed view of FIG. 15.

Referring to FIGS. 14 and 15, the pivoting arm 50 is rotatably connected to the pivot point 52 by means of a conical bearing 78, or any suitable type of bearing.

The motors 62, 68 used are preferably brush type DC motors coupled to pulse width modulation (PWM) type amplifiers. Of course, any suitable type of motors may be used.

Figure 18:
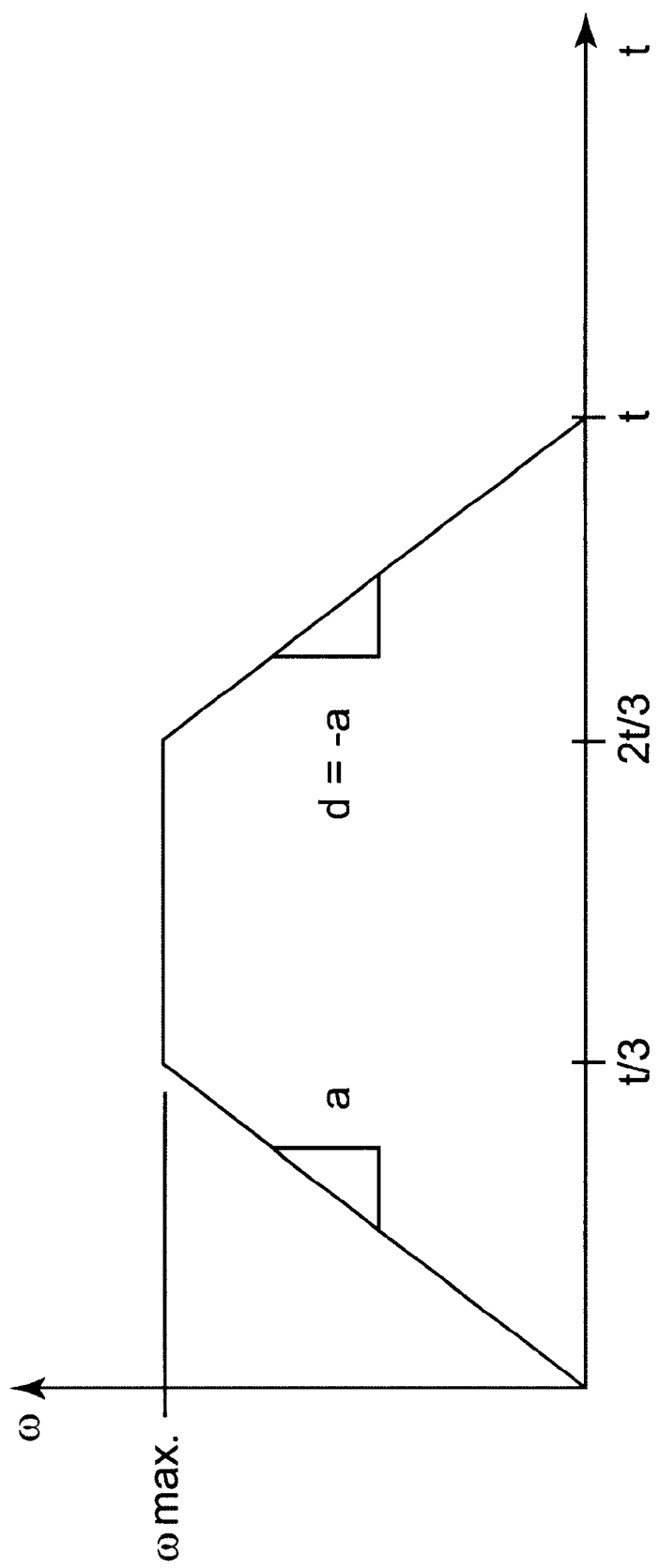
FIG. 18 is graphic representing of the speed of the motors.

Referring to FIG. 18, the most commonly used method for effecting a delta displacement from point-to-point is the trapezoidal profile. In such a profile, the acceleration and deceleration times and plateau times are all equal. Of course, other profiles may be used depending on design preferences. In fact, the profile may also be a complex function. This is useful in order to define a specific type of movement of the camera support and the camera itself. This aspect of the invention is related to the example above wherein the camera support and camera may describe a pattern in space (e.g. S-shaped) and still focus the target.

In order to accurately position the pivoting arm 50 and camera 46, it is necessary to include a feedback position system on each of the segments of the arm. The most common methods used for encoding angular or linear position of a mechanical moving structure are an optical encoder (accurate), a potentiometer (less accurate), or a resolver (very accurate). The signals of these encoders are interpreted by a microcontroller, and if their output signals are analog, these must be converted into digital signals. Thus, the potentiometer and resolver are connected to an analog to digital converter and the optical encoder is coupled to a counter. The present system may comprise potentiometers only.

The acquisition card DAQcard-1200 of National Instrument is used as a analog to digital converter of 12 bits (2096 incremental positions). Tests have shown that there is a loss of about 2 bits in the analog to digital conversion.

Figure 19:
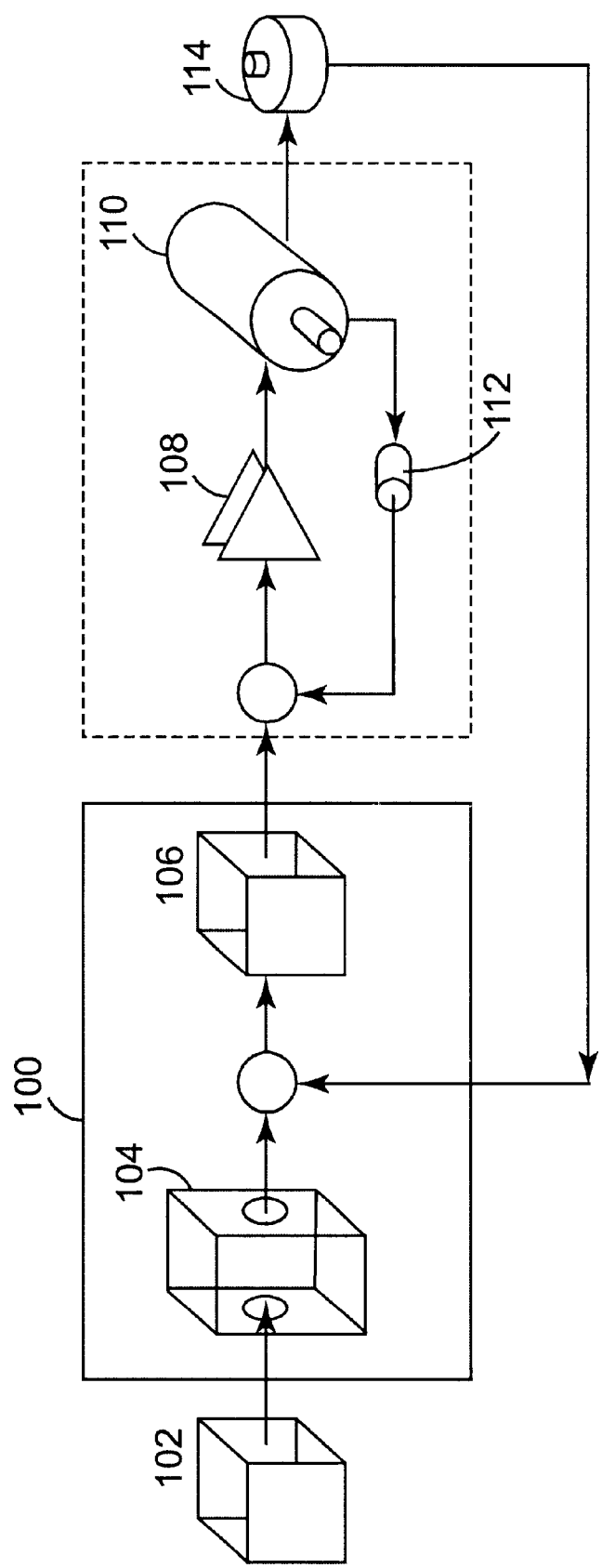
FIG. 19 is a block diagram illustrating the control of the motors.

Referring to FIG. 19, there is shown a simplified block diagram of the operation of the controllable camera support system and the camera system. A motion controller 100 receives the instructions from an interface 102. The interface 102 includes a computer system (such as a PC) for receiving measured rotational and radial positions from the sensors. As previously discussed the sensors may be position sensor or speed sensors depending on design preference. The interface 102 also comprises a user interface (such as a computer screen, keyboard and mouse) which is coupled to the computer system for generating a position and/or speed command signals. The program 104 running on the computer system and which permits the user to position the camera support as well as the camera angle and focus will be described later on. With this program, the computer generates the position and/or speed command signals that are sent to a controller 106. Of course, the controller 106 may be in the computer system or indirectly coupled to it.

Command signals from the motion controller are sent to an amplifier 108 and to DC motors 110 (which may be servo-motors having a feedback tachymeter 112). The servo-motor 110 is further monitored by an encoder 114. Feedback mechanisms in position and/or speed are added to the system. Open loop systems called feed forward controllers may be used in combination with closed loop controllers, such as the Proportional Integral Derivative (PID) controllers. The sensors most commonly used in feedback systems are the encoders, resolvers, tachymeters and potentiometers.

By sampling sensor readings, the position of the camera support is continuously known. The controller may thus be able to modify the command signals in order to make corrections in real time of the position and/or speed of the system.

Figure 20:
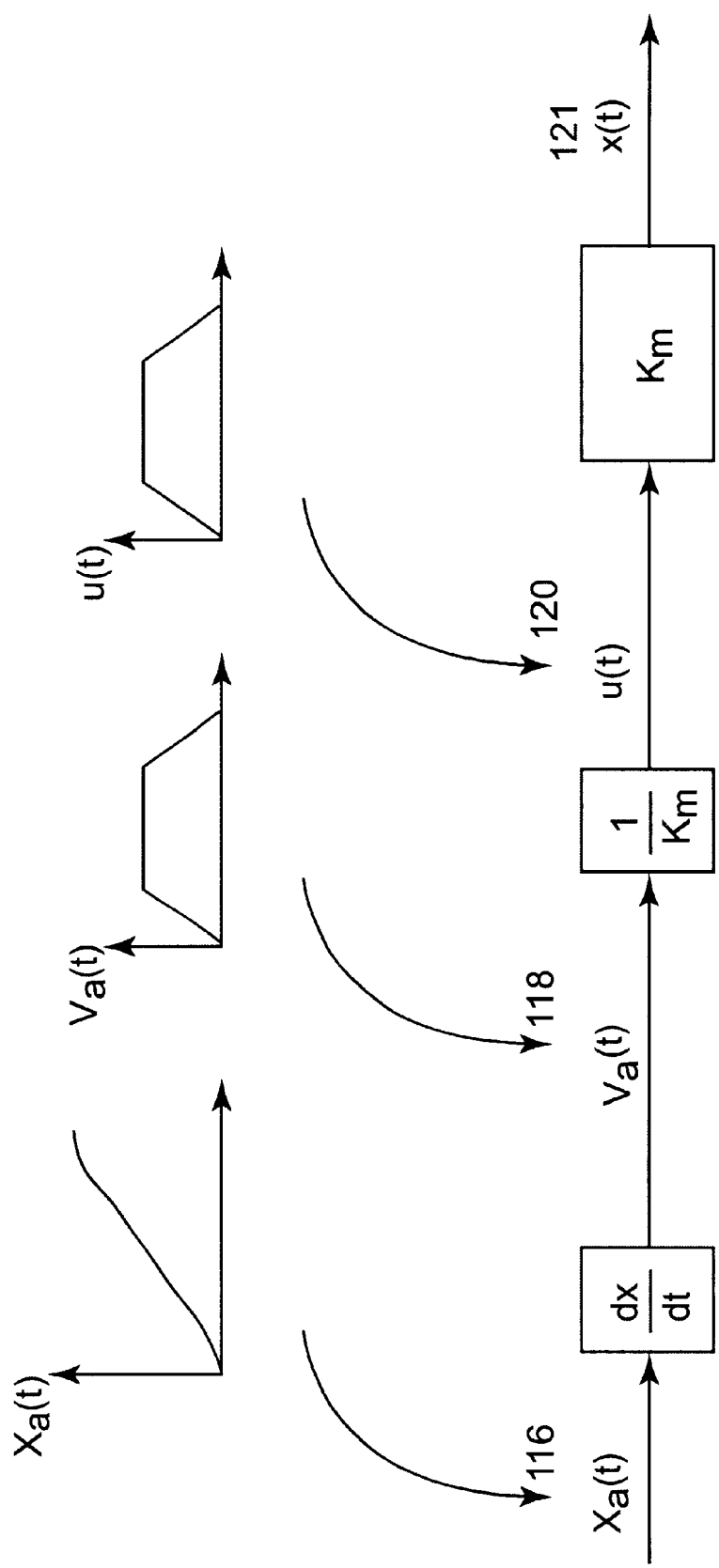
FIG. 20 is a block diagram of an feed forward controller.

Referring to FIG. 20, there is shown an feed forward controller (open loop). Known feed forward controllers are used with step motors. The controller sends a series of impulsions to the amplifier. The position and speed of the system are predetermined by the series of impulses sent to the motor. The precision and flexibility of the feed forward controller is low because there is an accumulation of errors during the process. From the desired position signal 116, the speed 118 and a control command 120 are calculated. Km represents the gain of the manipulator which provides the real position signal 121.

Figure 21:
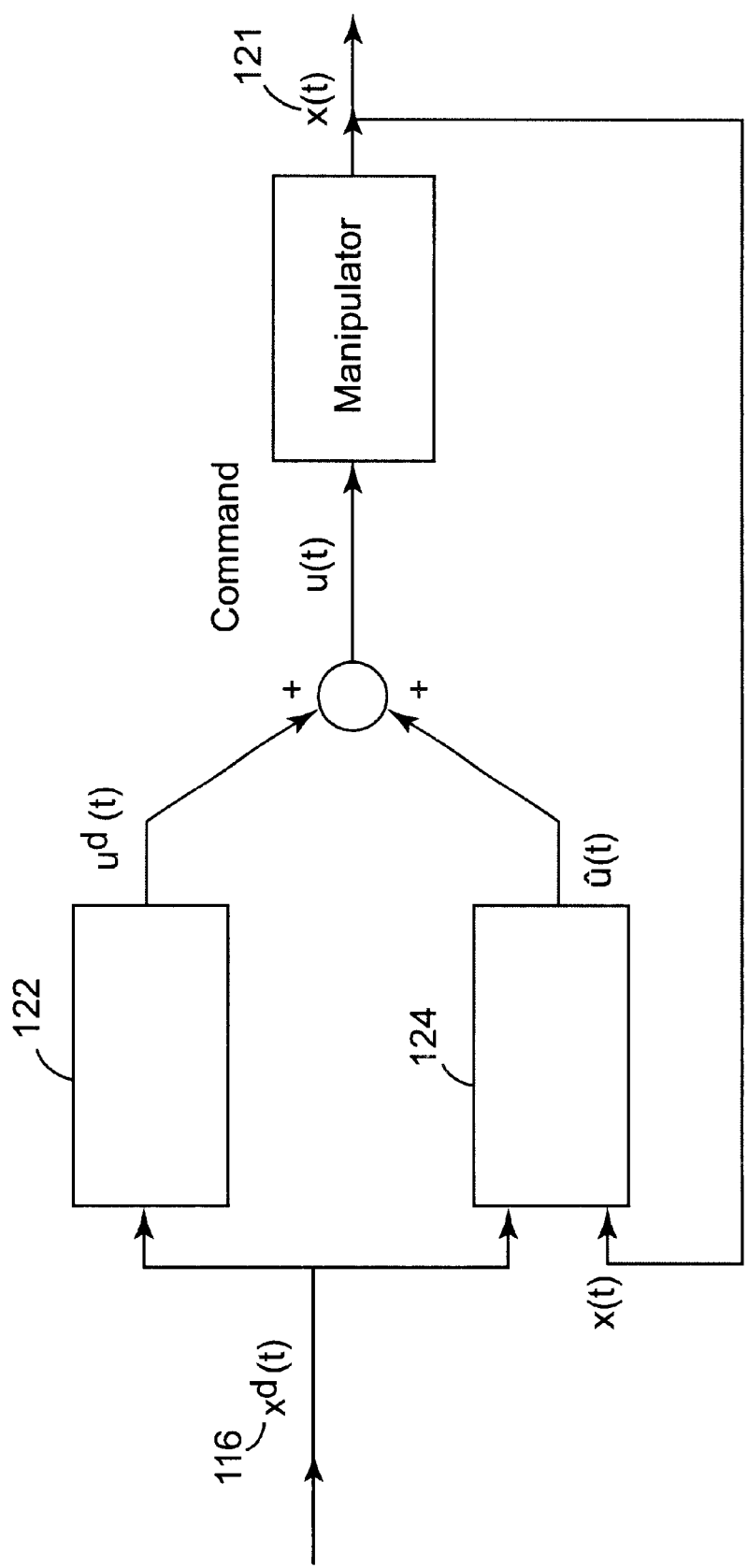
FIG. 21 is a block diagram of a controller.

Referring to FIG. 21, the feed forward controller 122 is coupled to a feedback or corrective action controller 124. The basic operating principle of the resulting controller is to provide the speed and position profiles for all degrees of freedom of the system so as to properly synchronize all movements of the system parts and to enable the moving of the camera position's "point of view" while always fixing the "viewing target" throughout the movements of the system. Somple trapezoidal profiles can be used when changing viewing targets or for less accurate movements.

Figure 22:
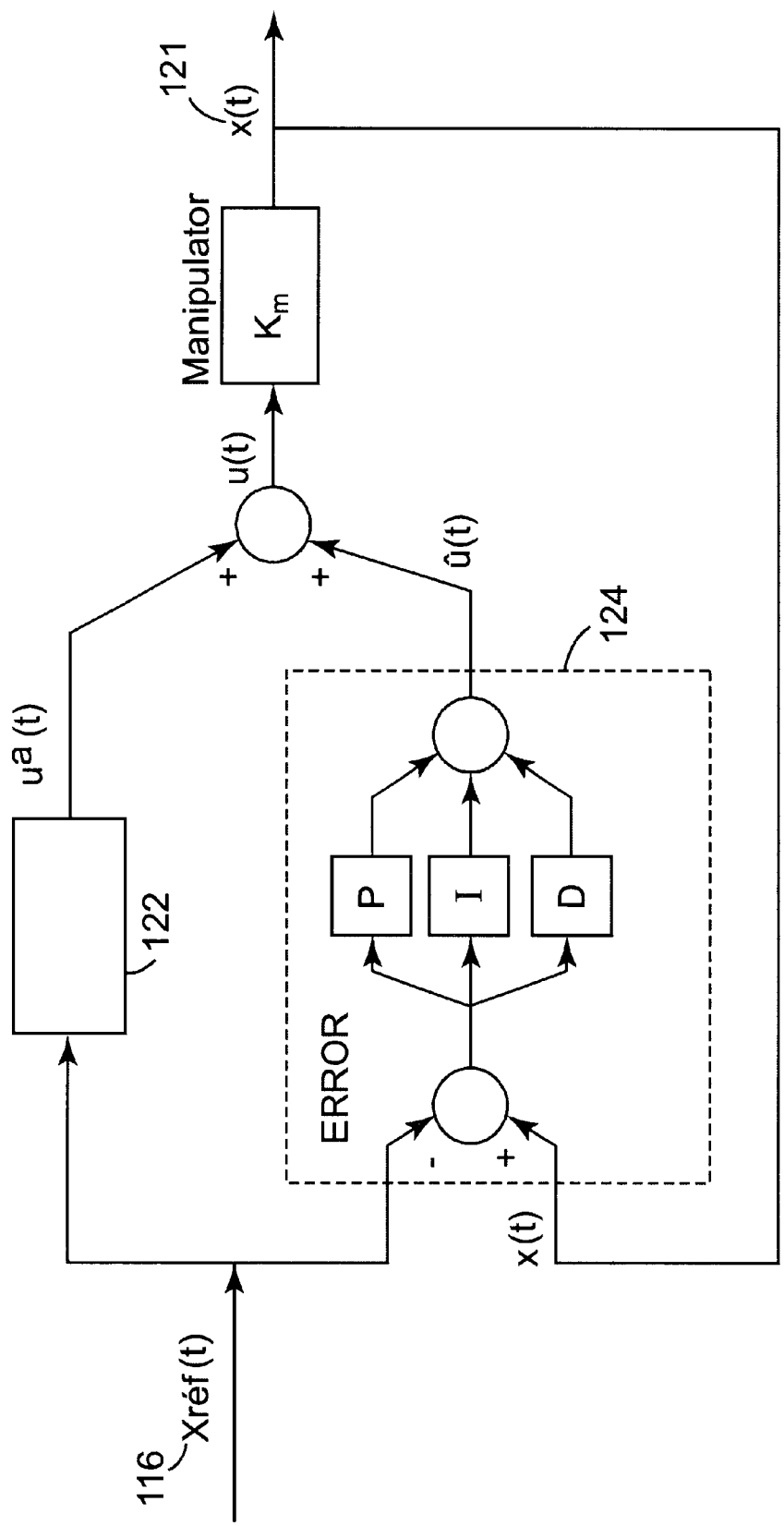
FIG. 22 is a block diagram of a controller.

Referring to FIG 22, there is shown a typical control system using the feed forward controller 122 and a feedback controller 124 (PID controller).

Figure 23:
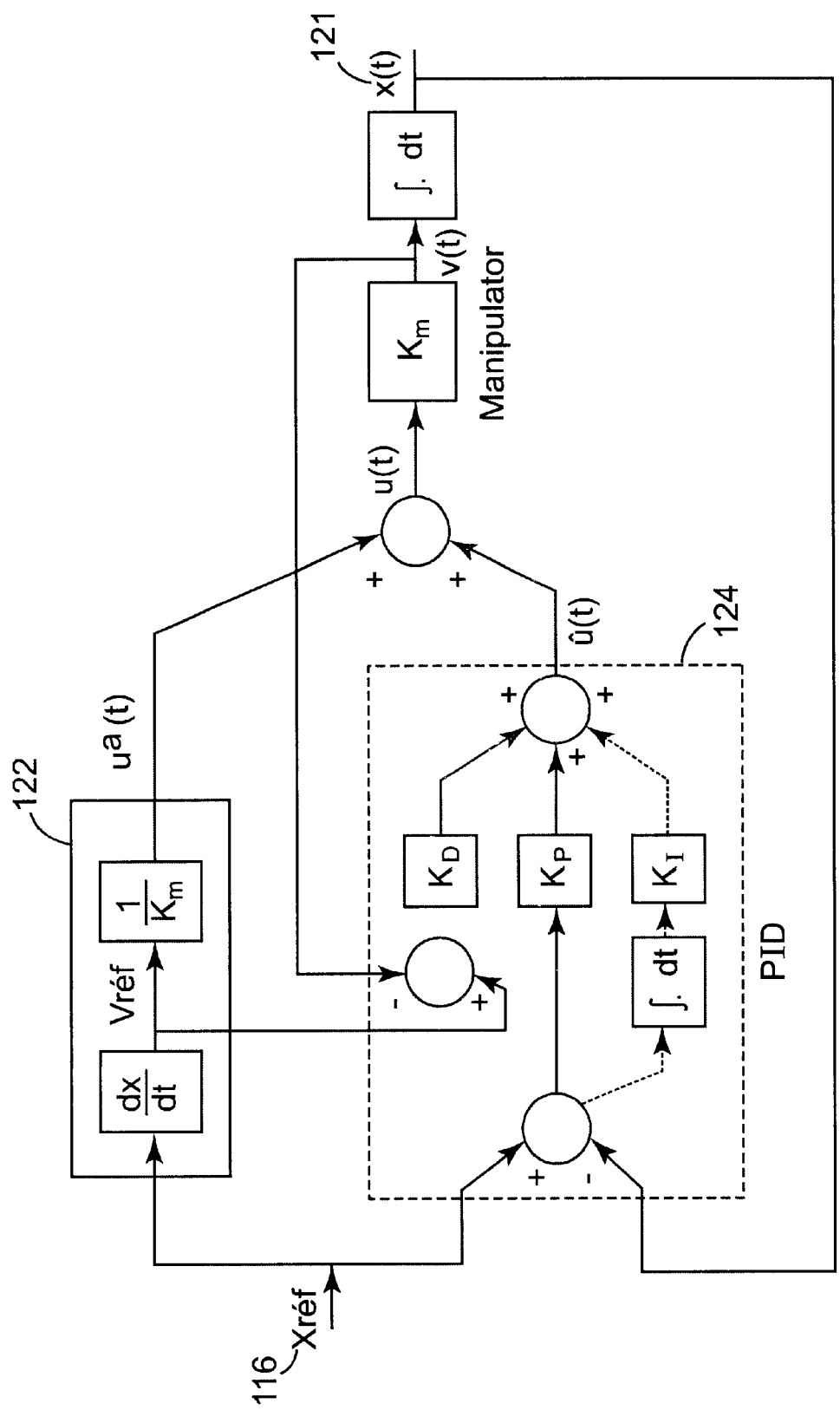
FIG. 23 is a block diagram of a controller according to a preferred embodiment of the invention.

Referring to FIG. 23, there is shown the preferred configuration of controllers used in the present system. The PID controller 124 has been slightly modified and the integration part is done at the end of the control loop. The feedback controller 124 is thus a PD controller without the I.

The position control is calculated from a speed profile (feed forward controller 122) and uses feedback on both position and speed of the system. These speed and position profiles are then fed into the feed forward controller, while the corrective action controller ensures that the profiles are respected by the system.

The feed forward controller sends the anticipated commands to the manipulator while the corrective action controller ensures that the anticipated speed and position profiles are respected.

Figure 24A:
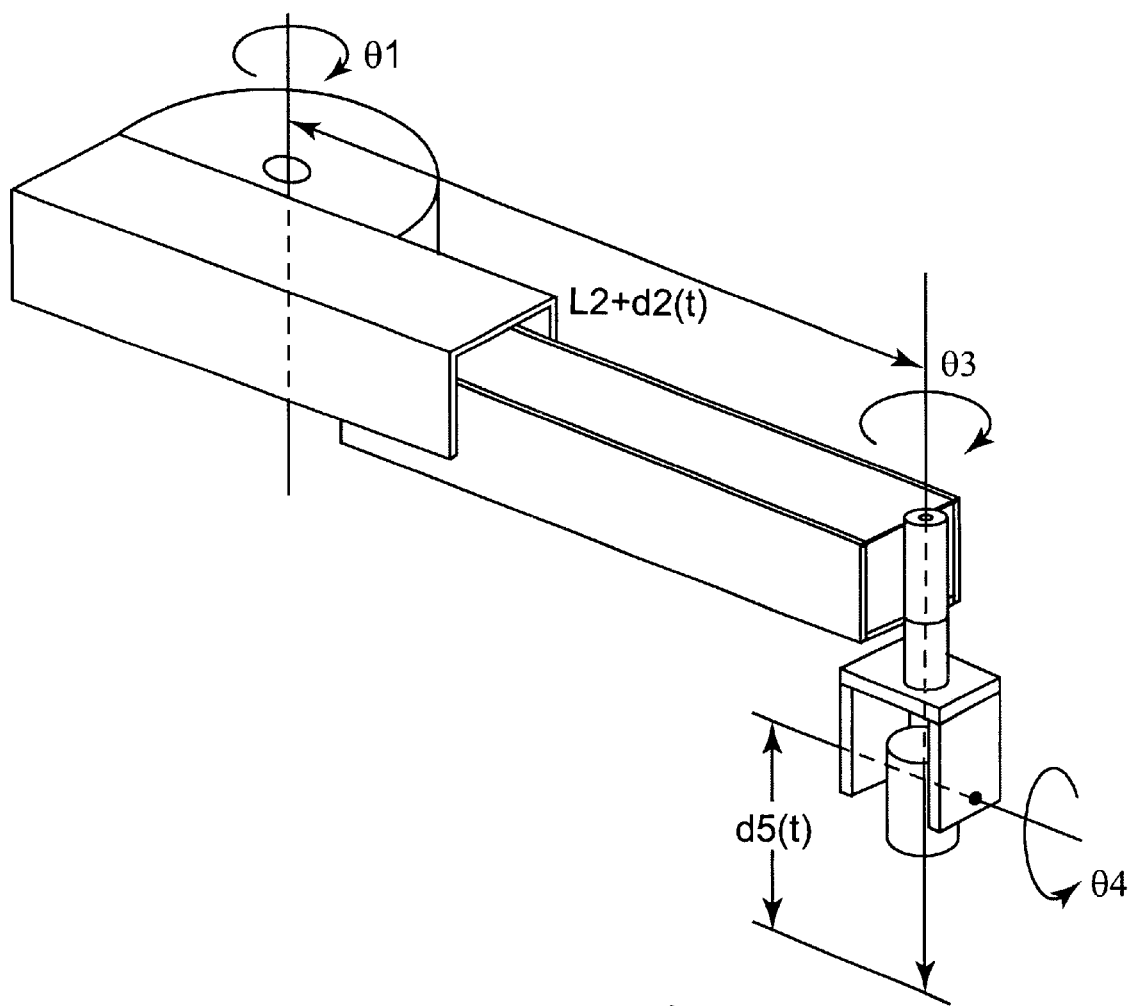
FIG. 24 is a perspective view of the camera support and its control parameters.
Figure 24B:
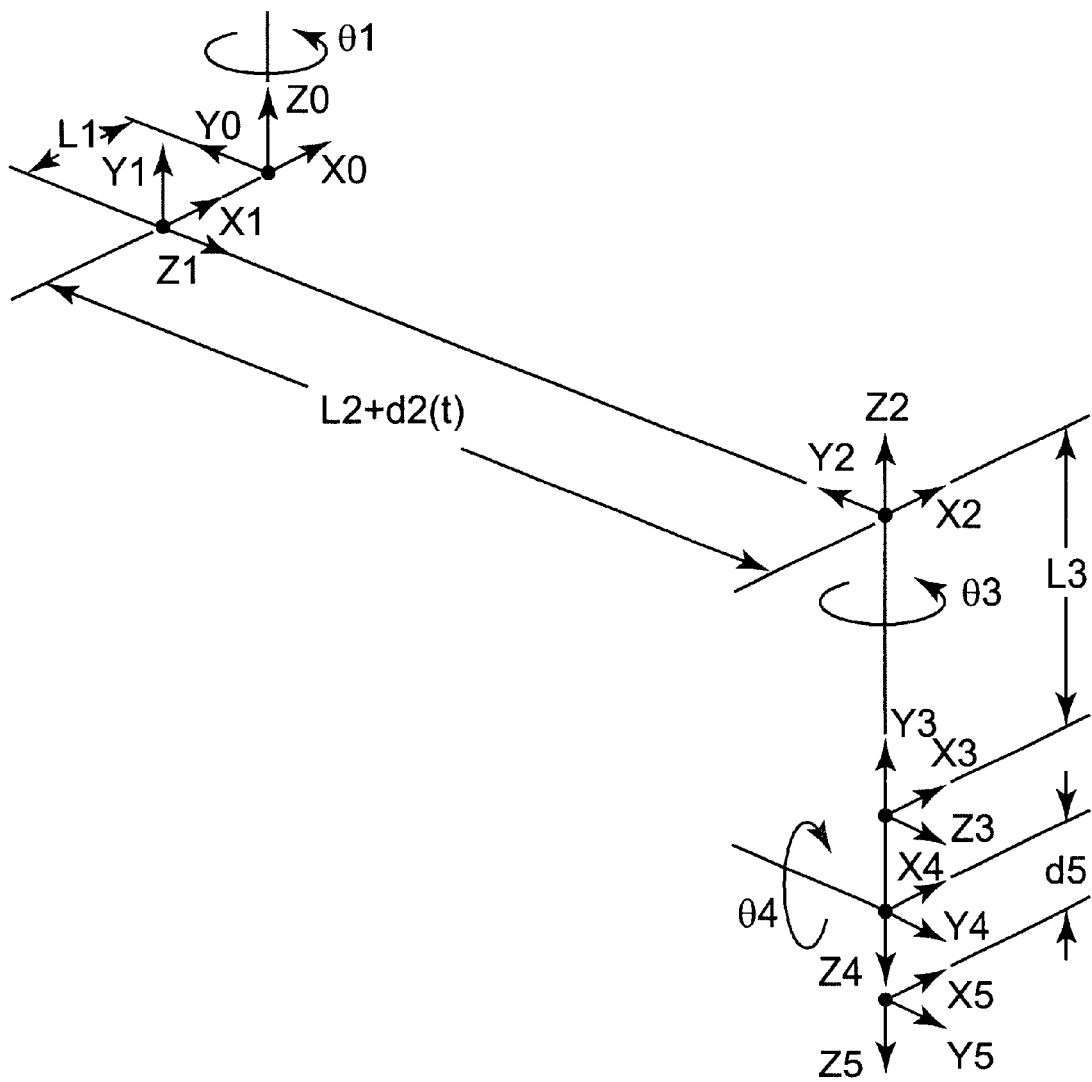
Figure 25:
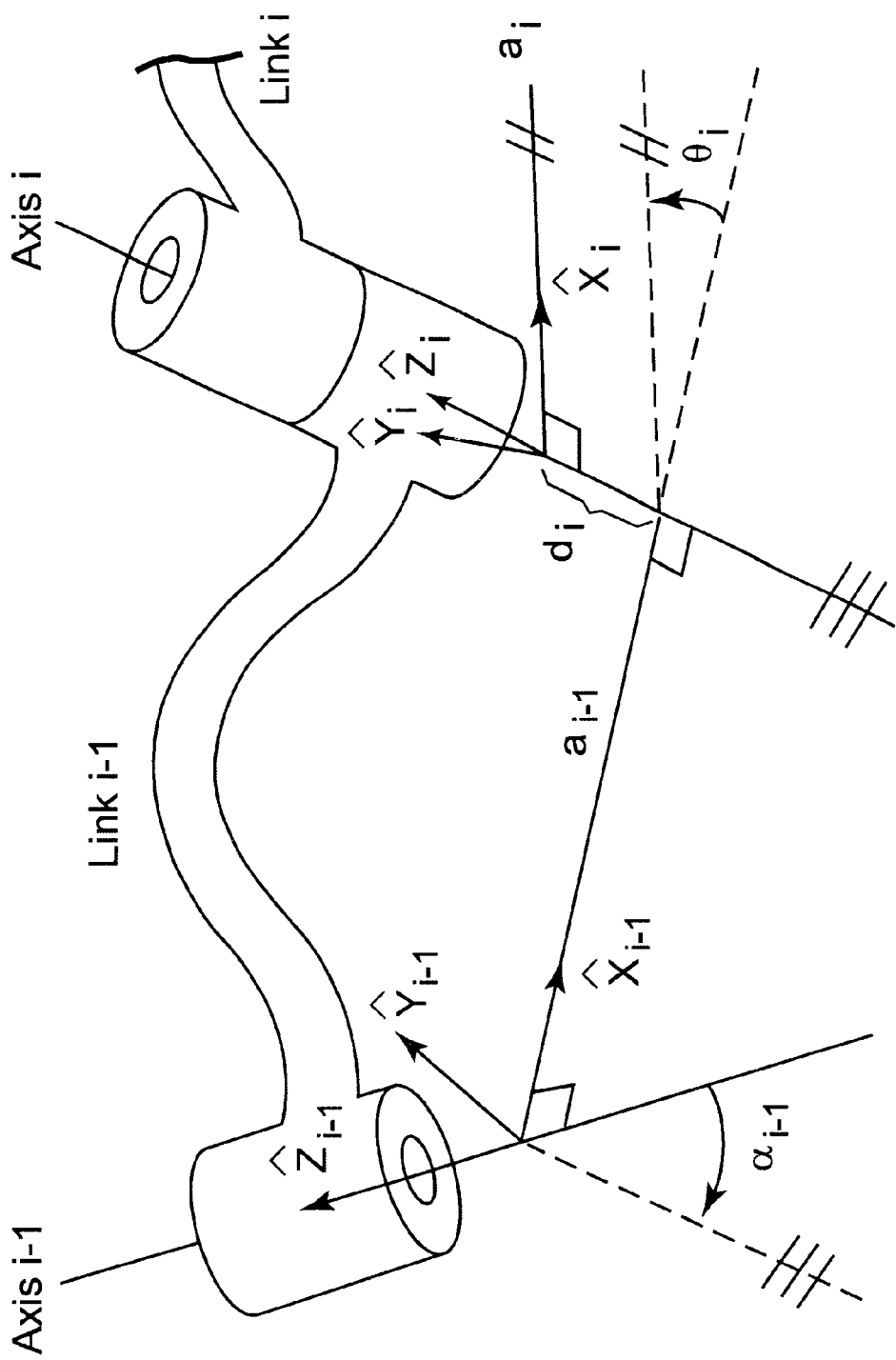
FIG. 25 is schematic view of the parameters of the camera.

Referring to FIGS. 24 and 25, there is shown the camera support and the different variable parameters of the system. The parameters of the Denavit Hartenberg of the present system are shown in FIG. 26.

The inverse kinematics may be calculated using different methods. The geometrical method is used in the present system because it is simpler than the algebraic method. The inverse kinematics of the system is used to calculate the desired moving trajectories.

Figure 27:
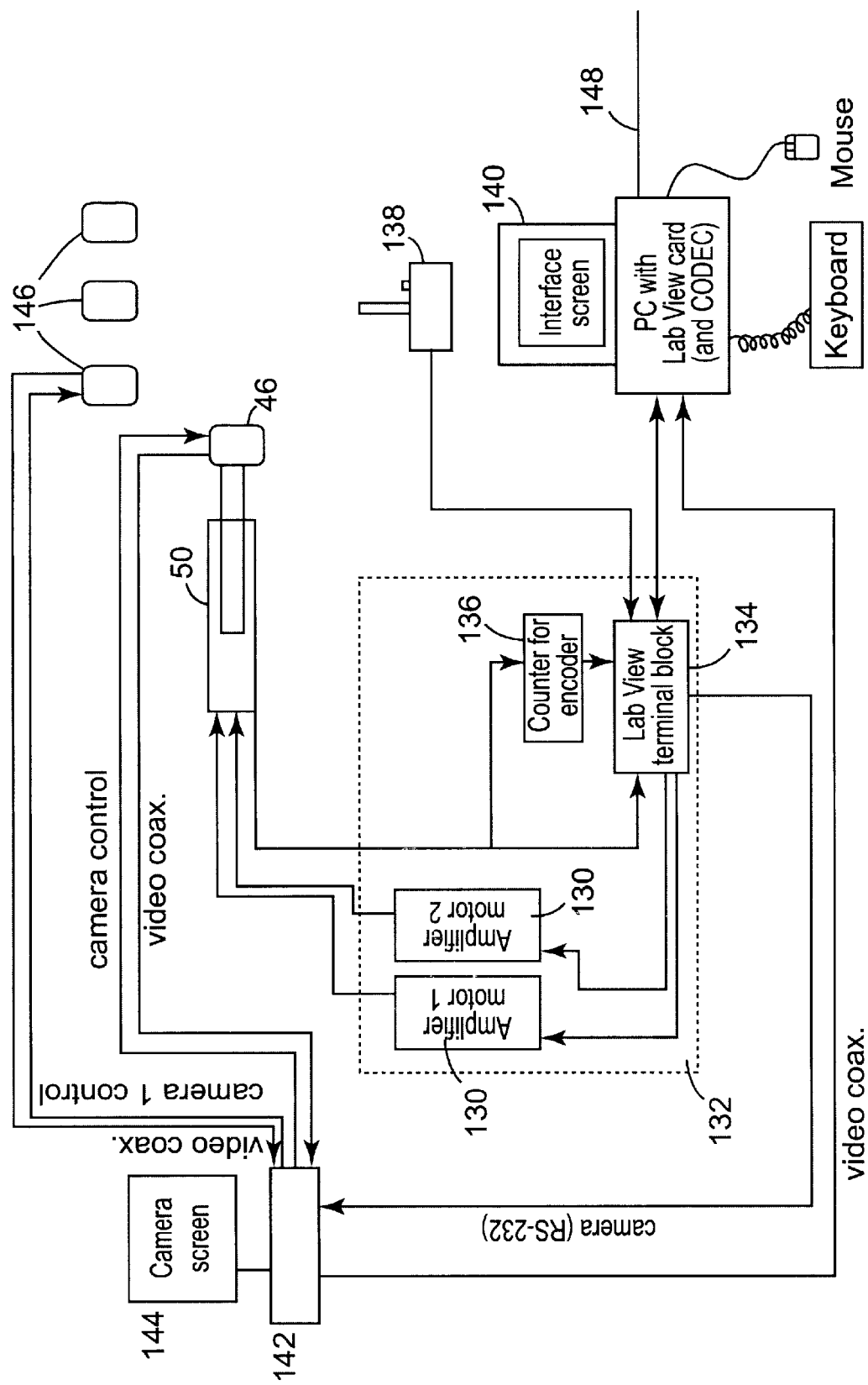
FIG. 27 is a block diagram of the camera system according to a preferred embodiment of the invention.

Referring to FIG. 27, there is shown a schematic bloc diagram of the camera system according to a preferred embodiment of the present invention. As shown before, the pivoting arm 50 is connected to the camera 46. The motors inside the pivoting arm are powered by amplifiers 130, which are inside a command unit 132. The command unit 132 also comprises a LabView™ connector 134 for sending control commands to the amplifiers 130. The command unit 132 also comprises a counter 136 of an encoder which is coupled to the pivoting arm 50. The LabView™ connector 134 receives signals from the counter 136. The LabView™ connector 134 also is connected to a control joystick 138 for manual control of the pivoting arm 50. The LabView™ connector 134 is further connected to a computer system or PC 140 including a LabView™ card and a CODEC card, a computer screen, a keyboard and a mouse. The PC 140 is connected to a command module 142 of the camera 46. A local camera screen 144 is connected to the command module 142. The command module 142 is adapted to send commands directly to the camera 46 for operation thereof through coaxial cables. The command module 142 is also connected to another camera 146 or to several other cameras 146.

In use, a user observes the activities in the operating room 10 from a screen 144 connected to the camera. The user may control the position of the camera directly by means of the joystick, or indirectly by means of the PC 140.

The pivoting arm 50 and the camera 46 are both controlled by the PC, which contains the control software and the acquisition card. Commands are sent from the PC 140 to the command unit 132, which processes the received signals. Part of the command signals are sent to the amplifiers 130 for operating the motors. Other command signals are sent to the camera command module 142 through a RS-232 interface.

The command unit 132 powers the potentiometers and limit switches in the pivoting arm 50. The information received from the potentiometer, encoders and limit switches, and information received from the camera (tilt, azimuth, focal adjustment) is sent to the PC 140. The PC 140 may be connected to a network 148 (by using a CODEC card for example).

The joystick 138 controls the operation of the two motors of the pivoting arm 50. It includes an emergency button to shut down the system in case of emergency. The joystick 138 may be used independently without the PC 140.

A user interface is provided for sending commands to camera system through the controller. The camera system has 4 degrees of freedom ($\theta_1$, Lv, $\theta_3$, and $\theta_4$), and an extra virtual degree of freedom, the focal distance F. While positioning the camera, each of the five aforementioned parameters must be adjusted. The manual displacement of all of these parameters is a difficult task, but it is very easy for a robotic computer assisted system.

Figure 28:
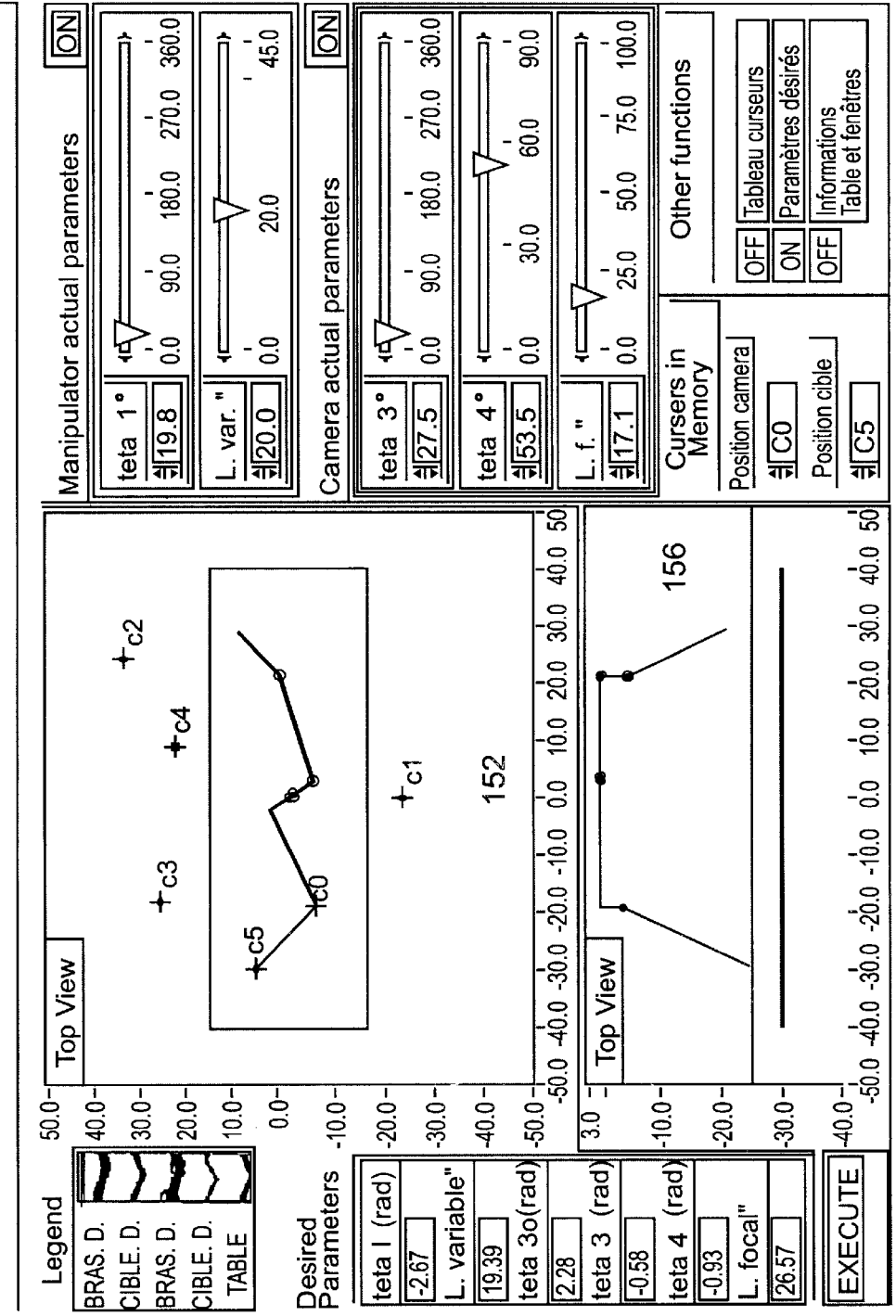
FIG. 28 is a schematic view of a graphical interface of the system.
Figure 29:
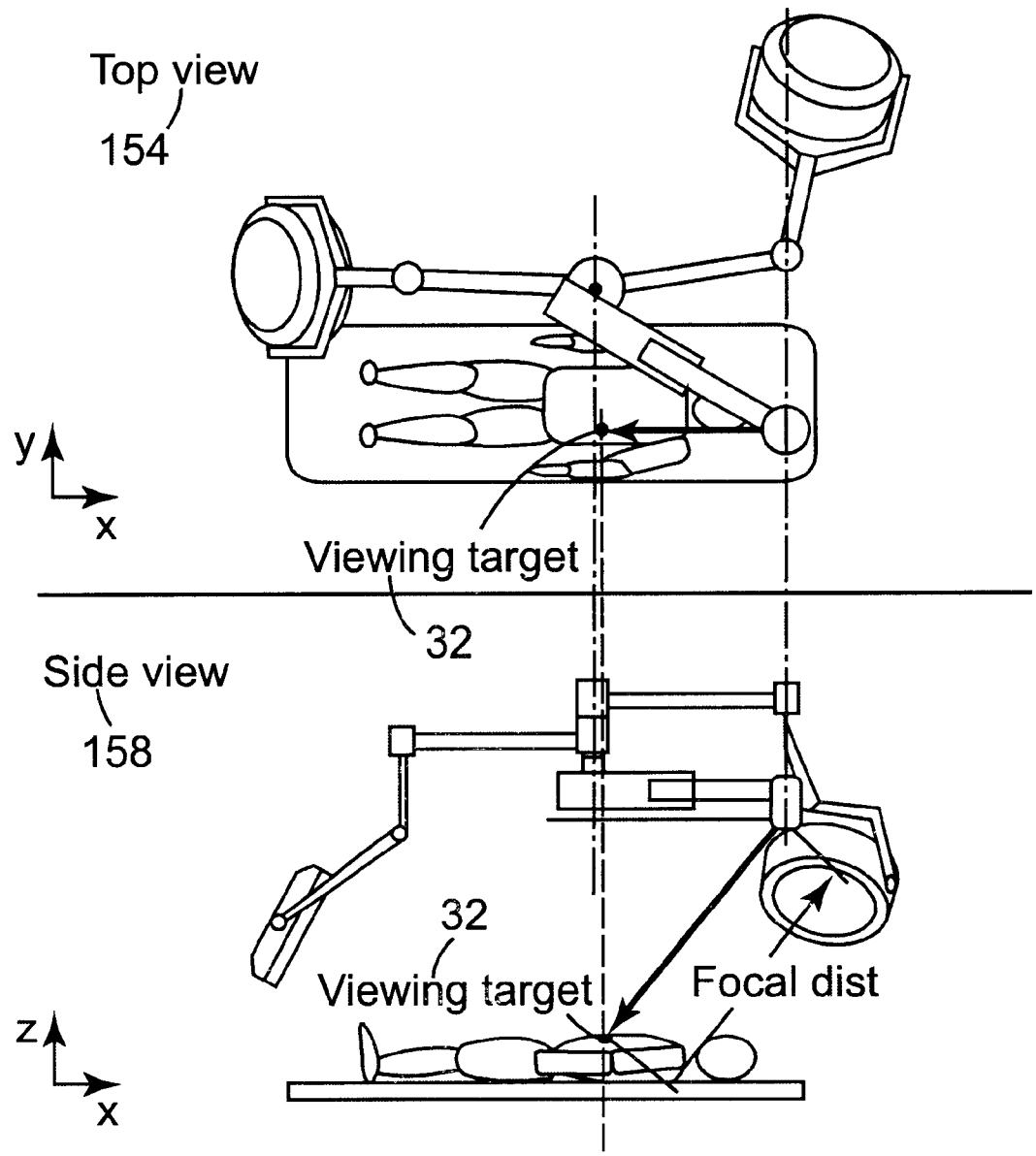
FIG. 29 are top and side views of the camera system.

Referring to FIGS. 28 and 29, a graphical interface 150 shown in FIG. 28 corresponds to the physical system shown in FIG. 29. A first window 152 of the graphical interface 150 corresponds to a top view 154 shown in FIG. 29. A second window 156 of the graphical interface 150 corresponds to a side view 158 shown in FIG. 29.

The top view 154 allows to locate objects in a plane (x and y), whereas the side view brings in height information (z). The tri-dimensional position of the target 32 may be translated in the aforementioned robotic parameters: 1, Lv, 3, 4 and F.

Figure 30:
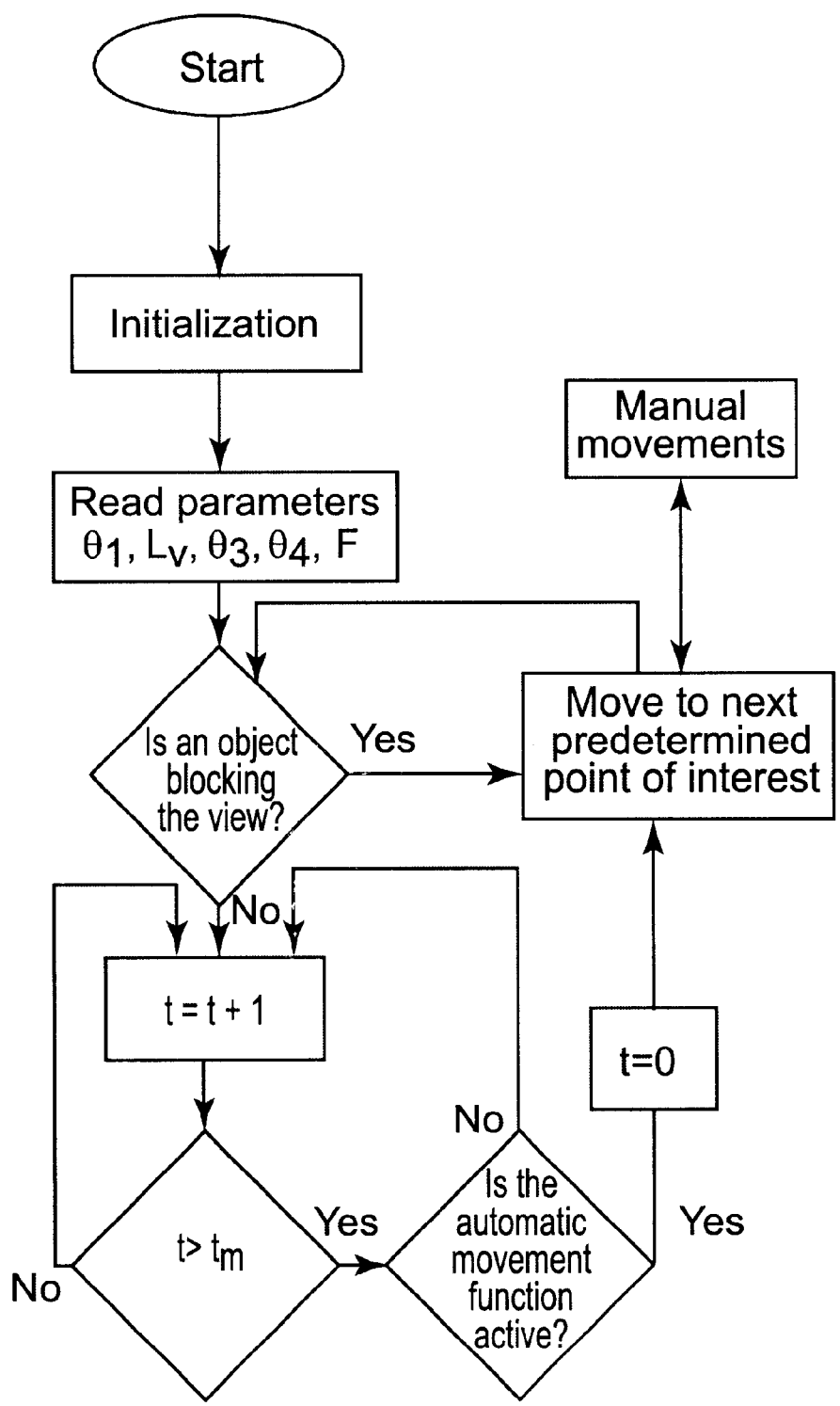
FIG. 30 is a flow diagram of an operation of the controllable camera.

Referring to FIG. 30, there is shown an algorithm for controlling the camera system when the target becomes obstructed by an obstruction. The control system is adapted to move the camera to another predetermined position all the while focusing on the target as previously explained. Thus, the camera can be moved to another predetermined position where the obstruction does not obstruct the camera.

Also included in the algorithm is a function that automatically moves the camera if a certain time tm has been reached, thus providing another view point.

Figure 31:
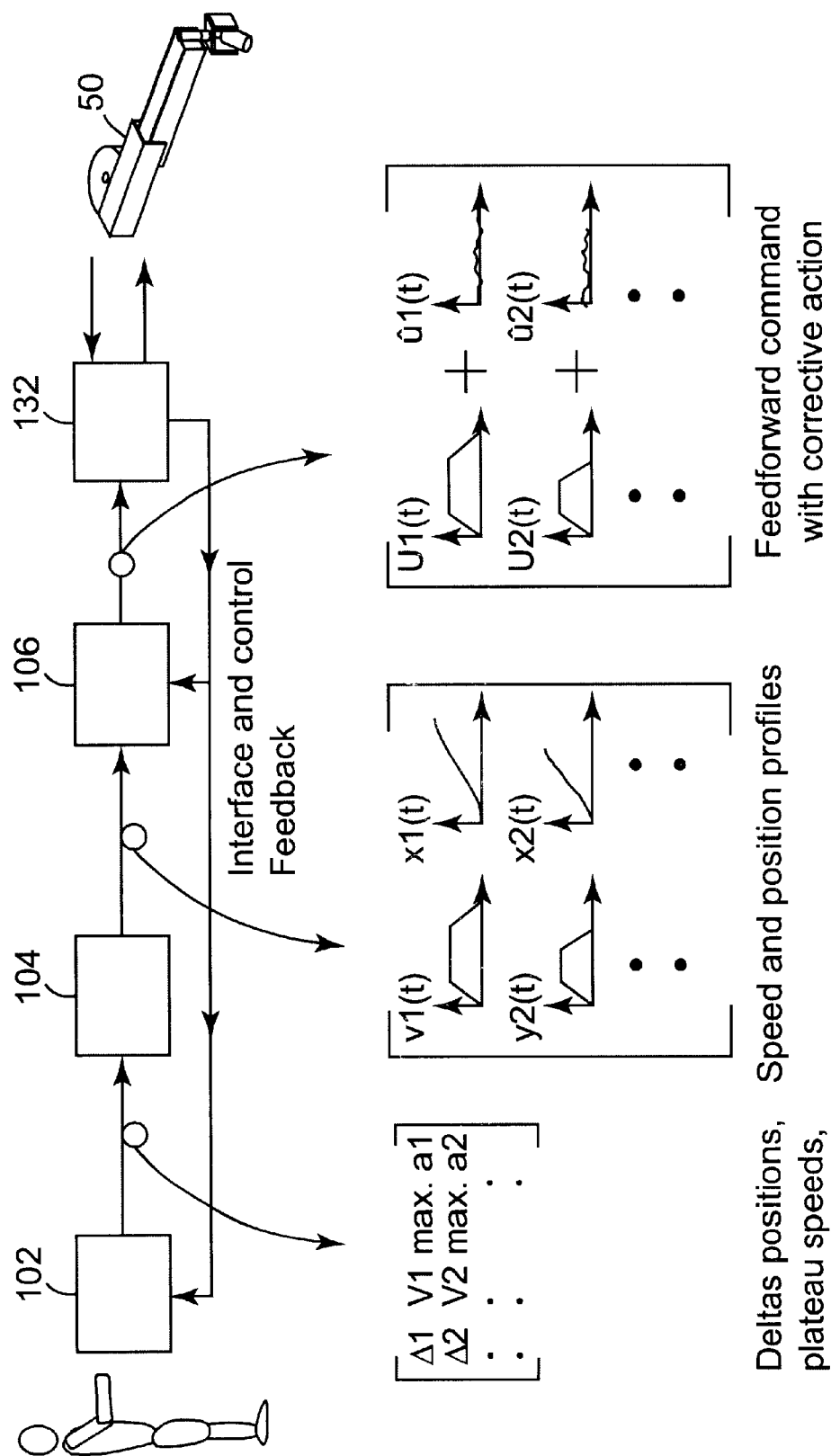
FIG. 31 is a block diagram of the main components of the system.

Referring to FIG. 31, there is shown a schematic block diagram of the principal operations of the system: the interface program 102 calculates the moving trajectories of the system according to the speed and position profiles 104. The controller 106, the command unit 132 and the pivoting arm 50 are also shown.

The graphical interface 150 shown in FIG. 28 may be separated in two parts: the real parameters and the desired parameters. The real parameters are directly provided by the acquisition card and from the system, thereby providing a continuous real position of the pivoting arm 50 and camera 46. From the direct kinematics equations, these real parameters are converted in real graphical displays showing top and side views of the system.

The desired parameters are shown on the left side of the graphical interface 150. Markers identified by "+" (1, 2, 3, 4, 5) represent the position of the camera 46 and the target 32.

The graphical interface 150 is adapted to receive the commands of the user to control the camera and its support. These commands may be sent directly with the help of a mouse, by moving the markers around the screen. The moving of the markers triggers an automatic calculation of the desired parameters by the system on the interface 150. The desired parameters are calculated from the inverse kinematics equations to generate the desired trajectories (at the end of which we obtain the desired end position).

When a user moves a marker in both the side view and top view, a command is sent to reposition the camera.

Predetermined views and targets may be stored in memory for allowing the user to switch between each of these points and perspectives. These memorized points are represented by the targets.

The present system may maintain the camera pointed to the same target for a certain period of time. When the target is stored in memory (as a virtual point in space), one can move the pivoting arm while still pointing the camera to the same spot or target.

Although preferred embodiments of the present invention have been described in detail herein and illustrated in the accompanying drawings, it is to be understood that the invention is not limited to these precise embodiments and that various changes and modifications may be effected therein without departing from the scope or spirit of the present invention.

What is claimed is:

1. A camera system comprising:

a pivoting arm adapted to be rotatably connected to a pivot point defining a first rotational axis, said pivoting arm defining a radial axis;

a camera holder mounted on said pivoting arm, said camera holder being displaceable along said radial axis;

a focal adjustable, rotational, tilting camera mounted on said camera holder, said camera defining a second rotational axis parallel to said first rotational axis about which said camera may rotate by means of a camera rotation motor, said camera defining a third rotational axis perpendicular to said first rotational axis about which said camera may tilt by means of a camera tilting motor, said camera including a focal adjustment mechanism, said camera focusing on a target;

motor means coupled to said pivoting arm and to said camera holder, said motor means adapted to impart rotational and radial motions to said camera holder; and control means for controlling said motor means, said camera rotation motor, said camera tilting motor, and said focal adjustment mechanism;

wherein when the target focused by the camera becomes obstructed by an obstruction, said control means is adapted to move said camera to another position all the while focusing on said target, whereby as said camera moves, said target is always focused by said camera so that said camera can be moved to another position where the obstruction does not obstruct said camera.

2. The camera system of claim 1, wherein said pivoting arm comprises at least first and second portions, said first portion being connected to said pivot point, and said second portion being adapted to effect a relative movement with respect to said first portion along said radial axis.

3. The camera system according to claim 2, wherein said pivoting arm comprises at least one additional portion adapted to effect a relative movement with respect to said first and second portions, thereby forming a telescoping arm.

4. The camera system according to claim 2, wherein said first portion has first and second extremities, said second portion has first and second ends, said first portion being connected to said pivot point near said first extremity, said camera holder being mounted on said second portion near said second end thereof, thereby defining a maximum distance between said pivot point and said camera holder.

5. The camera system according to claim 4, wherein said pivoting arm is rotatably connected to said pivot point by means of a conical bearing or any suitable type of bearing.

6. The camera system according to claim 5, wherein said motor means comprises:

a radial motor and an endless screw mechanism for sliding said first portion with respect to said second portion of the pivoting arm; and a rotational motor for rotating said pivoting arm.

7. The camera system according to claim 6, wherein the rotational motor comprises a slip clutch mechanism for disengaging said rotational motor from said pivoting arm.

8. The camera system according to claim 7, wherein the radial motor and endless screw mechanism are coupled to said slip clutch mechanism for disengaging said radial motor from said endless screw mechanism.

9. The camera system according to claim 6, further comprising limit switches connected to said radial and rotational motors, said limit switches adapted to shut down power to said motors before reaching a mechanical limit.

10. The camera system according to claim 6, wherein the motors are brush type DC servo-motors coupled to pulse width modulation (PWM) type amplifiers.

11. The camera system according to claim 1, wherein said control means comprises:

sensors coupled to said pivoting arm for measuring or calculating said rotational and radial motions thereof;

a computer means for receiving measured or calculated rotational and radial motions from said sensors;

a user interface coupled to said computer means for generating positioning and/or calculated speed and/or trajectory commands; and an open and/or closed loop control system for receiving said positioning and/or calculated speed and/or trajectory commands from said user interface and sending motor commands to said motor means.

12. The camera system according to claim 11, wherein said closed loop control system is a PID control system.

13. The camera system according to claim 1, wherein said control means comprises:

position sensors coupled to said pivoting arm for measuring rotational and radial positions thereof;

a computer system for receiving measured rotational and radical positions from said sensors;

a user interface coupled to said computer means for generating a position command signal;

an feed forward controller for generating a first output signal in response to the position command signal;

a differential controller for generating a second output signal in response to the position command signal and speed feedback signal;

a proportional controller for generating a third output in response to the position command signal and position feedback signal;

a treatment controller for generating said speed feedback signal in response to said output signals from the feed forward, differential, and proportional controllers;

an integral controller for generating said position feedback signal in response to the position feedback signal, for controlling said motor means.

14. The camera system according to claim 1, wherein the pivoting arm is adapted to be coupled with a surgical lamp system, said surgical lamp system having a receiving point connectable to said pivot point.

15. The camera system according to claim 1, wherein the pivoting arm is adapted to be mounted to a ceiling of a room to be inspected.

* * * * *